(12) United States Patent
Meade et al.

(10) Patent No.: US 6,673,333 B1
(45) Date of Patent: Jan. 6, 2004

(54) FUNCTIONAL MRI AGENTS FOR CANCER IMAGING

(75) Inventors: Thomas J. Meade, Altadena, CA (US); Scott Fraser, La Canada, CA (US); Russell Jacobs, Arcadia, CA (US)

(73) Assignee: Research Corporation Technologies, Inc., Tucson, AZ (US)

( * ) Notice: Subject to any disclaimer, the term of this patent is extended or adjusted under 35 U.S.C. 154(b) by 0 days.

(21) Appl. No.: 09/715,859

(22) Filed: Nov. 17, 2000

Related U.S. Application Data

(60) Provisional application No. 60/201,816, filed on May 4, 2000.

(51) Int. Cl.$^7$ ............................................. A61B 5/055
(52) U.S. Cl. ............................ 424/9.35; 424/9.363
(58) Field of Search ................... 424/9.3, 9.35, 424/9.36, 9.361, 9.363; 540/474

(56) References Cited

U.S. PATENT DOCUMENTS

| | | |
|---|---|---|
| 3,919,102 A | 11/1975 | Kühling et al. |
| 4,637,988 A | 1/1987 | Hinshaw et al. |
| 4,647,447 A | 3/1987 | Gries et al. |
| 4,678,667 A | 7/1987 | Meares et al. |
| 4,822,594 A | 4/1989 | Gibby |
| 4,837,169 A | 6/1989 | Toner |
| 4,877,872 A | 10/1989 | Morgan et al. |
| 4,885,363 A | 12/1989 | Tweedle et al. |
| 5,087,440 A | 2/1992 | Cacheris et al. |
| 5,095,099 A | 3/1992 | Parkinson et al. |
| 5,133,956 A | 7/1992 | Garlich et al. |
| 5,155,215 A | 10/1992 | Ranney |
| 5,188,816 A | 2/1993 | Sherry et al. |
| 5,219,553 A | 6/1993 | Kraft et al. |
| 5,230,883 A | 7/1993 | Kornguth et al. |
| 5,256,395 A | 10/1993 | Barbet et al. |
| 5,262,532 A | 11/1993 | Tweedle et al. |
| 5,292,414 A | 3/1994 | Sessler et al. |
| 5,310,539 A | 5/1994 | Williams |
| 5,322,681 A | 6/1994 | Klaveness |
| 5,332,567 A | 7/1994 | Goldenberg |
| 5,338,532 A | 8/1994 | Tomalia et al. |
| 5,358,705 A | 10/1994 | Boggs et al. |
| 5,407,657 A | 4/1995 | Unger et al. |
| 5,419,893 A | 5/1995 | Berg et al. |
| 5,428,156 A * | 6/1995 | Mease et al. ............... 540/474 |
| 5,446,145 A | 8/1995 | Love et al. |
| 5,466,438 A | 11/1995 | Unger et al. |
| 5,466,439 A | 11/1995 | Gibby et al. |
| 5,531,978 A | 7/1996 | Berg et al. |
| 5,554,748 A | 9/1996 | Sieving et al. |
| 5,565,552 A | 10/1996 | Magda et al. |
| 5,622,821 A | 4/1997 | Selvin et al. |
| 5,672,334 A * | 9/1997 | Ranney ..................... 424/9.34 |
| 5,707,605 A | 1/1998 | Meade et al. |
| 5,914,095 A | 6/1999 | Watson |
| 5,955,605 A | 9/1999 | Axworthy et al. |
| 5,980,862 A | 11/1999 | Meade et al. |
| 6,409,990 B1 * | 6/2002 | Vera ........................ 424/9.35 |

FOREIGN PATENT DOCUMENTS

| | | |
|---|---|---|
| CA | 2139374 A1 | 7/1995 |
| CA | 2182686 A1 | 8/1995 |
| CA | 2197074 | 2/1996 |
| WO | WO 90/12050 A1 | 10/1990 |
| WO | WO 92/19264 A1 | 11/1992 |
| WO | WO 94/03271 | 2/1994 |
| WO | WO 94/04485 | 3/1994 |
| WO | WO 95/10217 | 4/1995 |
| WO | WO 95/19185 | 7/1995 |
| WO | WO 95/19347 | 7/1995 |
| WO | WO 95/20353 | 8/1995 |
| WO | WO 95/27705 A1 | 10/1995 |
| WO | WO 95/28966 A1 | 11/1995 |
| WO | WO 95/31444 A1 | 11/1995 |
| WO | WO 95/32741 A1 | 12/1995 |
| WO | WO 96/05167 A1 | 2/1996 |
| WO | WO 96/23526 A2 | 8/1996 |
| WO | WO 96/38184 A2 | 12/1996 |
| WO | WO 97/01360 | 1/1997 |
| WO | WO 97/21431 A1 | 6/1997 |
| WO | WO 97/32862 A1 | 9/1997 |
| WO | WO 97/36619 A2 | 10/1997 |
| WO | WO 99/21592 A1 | 5/1999 |
| WO | WO 99/25389 A2 | 5/1999 |
| WO | WO 99/59640 | 11/1999 |
| WO | WO 01/08712 A2 | 2/2001 |
| WO | WO 01/52906 A2 | 7/2001 |
| WO | WO 01/82795 A2 A3 | 11/2001 |

OTHER PUBLICATIONS

Hubin et al., "Ultra rigid cross–bridged tetraaazamacrocyles as ligangs– the challenge and the solution," Chem. Commun., 1675–1676 (1998).

Hubin et al., "Crystallographic Characterization of Stepwise Changes in LIgand Conformations as Their Internal Topology changes and Two Novel Cross–Bridged Tetraazamacrocylclic Copper (II) Complexes," Inorg. Chem. 38:4435–4446 (1999).

Hubin et al., "New Iron (II) and Manganese (II) Compleses of Two Ultra–Rigid, Cross–Briged Tetraazamacrocyles for Catalysis and Biomimicry," J. Am. Chem. Soc. 122:2515–2522 (2000).

Weisman et al., "Cross–Bridged Cyclam. Protonation and Li$^+$ Complexation in a Diamond–Lattice Cleft," J. Am. Chem. Soc. 112:8604–8605 (1990).

Weisman et al., "Synthesis and tranxition–metal complexes of new cross–bridged tetraamine ligands," Chem. Commun., 947–948 (1996).

(List continued on next page.)

Primary Examiner—Michael G. Hartley
(74) Attorney, Agent, or Firm—Dorsey & Whitney LLP; Robin M. Silva; Renee M. Kossiak

(57) ABSTRACT

The invention relates to novel magnetic resonance imaging contrast agents for imaging cancer.

10 Claims, 5 Drawing Sheets

OTHER PUBLICATIONS

Wong et al., "Synthesis and Characterization of Cross–bridged Cyclams and Pendant–Armed Derivatives and Structural studies of their Copper(II) Complexes," J. Am. Chem. Soc. 122:10561–10572 (2000).

Jacobs and Fraser, "Magnetic Resonance Microscopy of Embryonic Cell Lineages and Movements," Science, 263:681–684 (1994).

Staubli and Meade, "The Design and Synthesis of Fluorescently Detectable Magnetic Resonance imaging Agents for Embryonic Cell Lineage Analysis," American Chemical Society: Division of Inorganic Chemistry, 209th ACS National Meeting, Anaheim, California, Abstract No. 385 (Apr. 2–6, 1995).

Aguayo, J.B., et al. "Nuclear Magnetic Resonance Imaging of a Single Cell," Nature, Letters to Nature 322:190–191 (Jul. 10, 1986).

Alexander, "Design and Synthesis of Macrocylic Ligands and Their Complexes of Lanthanides and Antinides," Chem. Review, 95:273–342 (1995).

Borch, R.F., et al. "The Cyanohydridoborate Anion as a Selective Reducing Agent," Journal of the American Chemical Society 93(12): 2897–2904 (Jun. 16, 1971).

Cho, Z.H., et al. "Some Experiences on a $4\mu\mu$m NMR Microscopy," Book of Abstracts, vol. 1, p. 233, Society of Magnetic Resonance in Medicine, 6th Annual Meeting and Exhibition, Aug. 17–21, 1987, New York City, NY.

Grynkiewicz, G., et al., "A New Generation of Ca2+ Indicators with Greatly Improved Fluorescence Properties," The Journal of Biological Chemistry, 260(6): 3440–3450 (1985).

Hennessy, M.J., et al., "NMR Surface Coil Microscopy," Book of Abstracts, vol. 2, p. 461–462, Society of Magnetic Resonance in Medicine, 5th Annual Meeting and Exhibition, Aug. 19–22, 1986, Montreal, Quebec, Canada.

Hoult, D.I., et al. "The Signal–to–Noise Ratio of the Nuclear Magnetic Resonance Experiment," Journal of Magnetic Resonance, 24: 71–85 (1976).

Jackels, "Section III: Enhancement Agents for Magnetic Resonance and Ultrasound Imaging. Chapter 20: Enhancement Agents for Magnetic Resonance Imaging: Fundamentals," Pharm. Med. Imag. Section III, Chap. 20, pp. 645–661 (1990).

Johnson, G.A., et al., "MR Microscopy at 7.0 T," Works in Progress, Society of Magnetic Resonance in Medicine, Sixth Annual Meeting and Exhibition, Aug. 17–21, 1987, New York City, NY. P.23.

Li, et al., "A Calcium–Sensitive Magnetic Resonance Imaging Contrast Agent," J. Am. Chem. Soc., 121:1413–1414 (1999).

Meade, T.J. et al., "Hydrophobic, Regiospecific Guest Binding by Transition–Metal Host Complexes Having Permanent Voids as Revealed by FT–NMR Relaxation Studies," J. Am. Chem. Soc., 108:1954–1962 (1986).

Meyer et al., "Advances in Macrocyclic Gadolinium Complexes as Magnetic Resonance Imaging Contrast Agents," Investigative Radiology, 25(1):S53–S55 (Sep. 1990).

Moats, et al., "A "Smart" Magnetic Resonance Imaging Agent That Reports on Specific Enzymatic Activity," Angew. Chem. Int. Ed. Engl., 36(7): 726–728 (Apr. 1997).

Moi, M.K., et al., "The Peptide Way to Macrocylic Bifunctional Chelating Agents: Synthesis of 2–(p–Nitrobenzyl) –1,4,7,10–tetraazacyclododecan– N, N", N"", N """–tetraacetic Acid and Study of Its Yttrium (III) Complex," J. Am. Chem. Soc. 110(18):6266–6267 (1988).

Nijhof, E.J., et al., "High–Resolution Proton Imaging at 4.7 Tesla," Proceedings of Soc. Magn. Reson. Med., P.925 (1987).

Runge, V.M., et al., "Future Directions in Magnetic Resonance Contrast Media," Top Magn. Reson–Imaging., 3(2):85–97 (1991).

Russell, E.J., et al. "Multicenter Double–Blind Placebo–Controlled Study of Gadopentetate Dimeglumine as an MR Contrast Agent: Evaluation in Patients with Cerebral Lesions," American Journal of Roentgenology, 152:813–823 (Apr. 1989).

Shukla, et al., "Design of Conformationally Rigid Dimeric MRI Agents," Magnetic Resoance in Medicine, 36(6): 928–931 (1996).

Sillerud, L.O., et al., "Proton NMR Microscopy of Inact Multicellular Tumor Spheroids," Book of Abstracts, vol. 1, p. 468, Society of Magnetic Resonance in Medicien, 6th Annual Meeting and Exhibition, Aug. 17–21, 1987, New York City, NY.

Tsien, R.Y. "New Calcium Indicators and Buffers with High Selectivity Against Magnesium and Protons: Design, Synthesis, and Properties of Prototype Structures," Biochemistry, 19(11): 2396–2404 (1980).

Tweedle, M.F., et al. "Considerations Involving Paramagnetic Coordination Compounds as Useful NMR Contrast Agetns," Nucl. Med. Bio. 15(1):31–36 (1988).

* cited by examiner

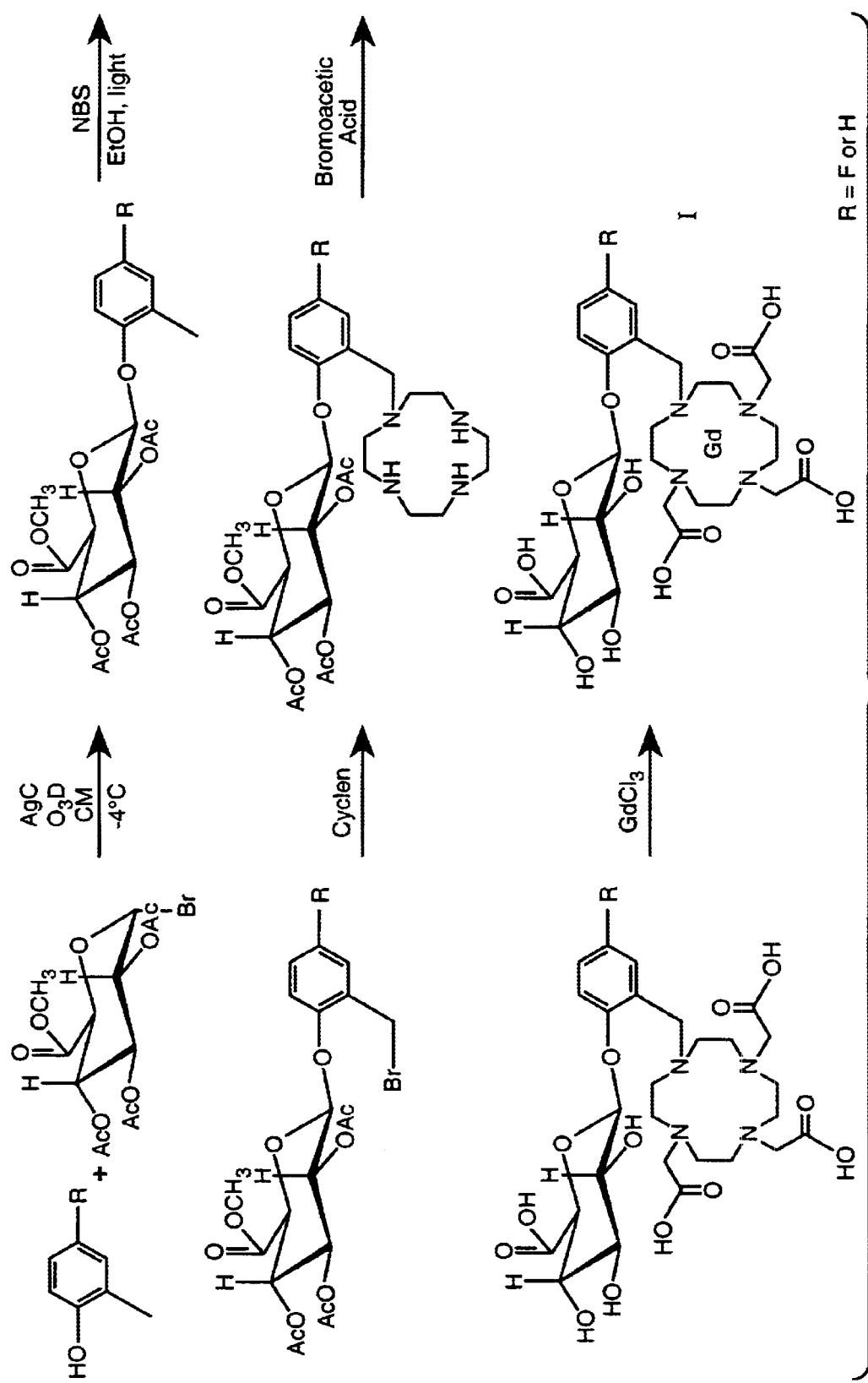
FIG._1

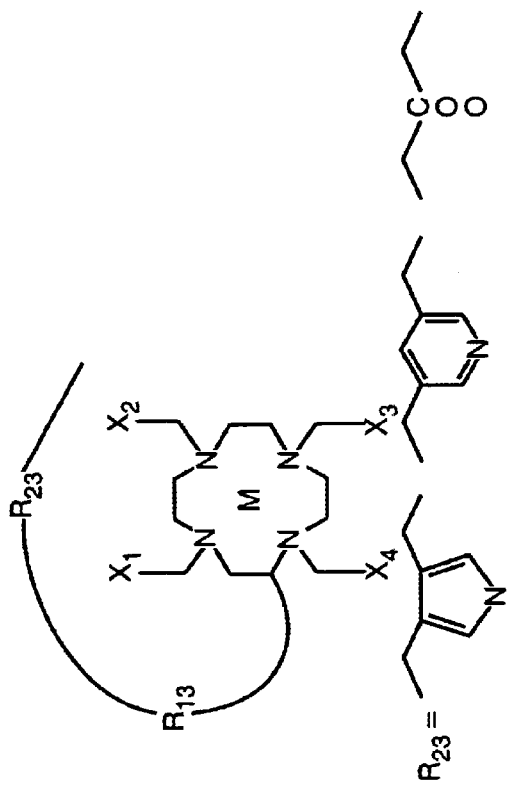
*FIG._4*
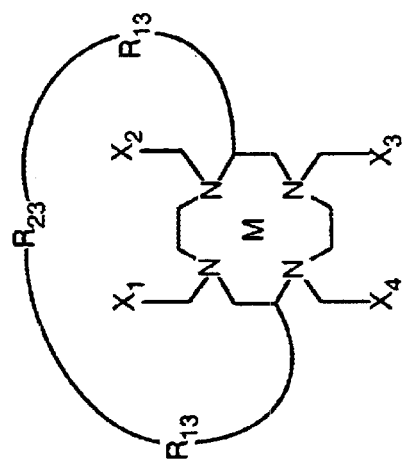
*FIG._5*
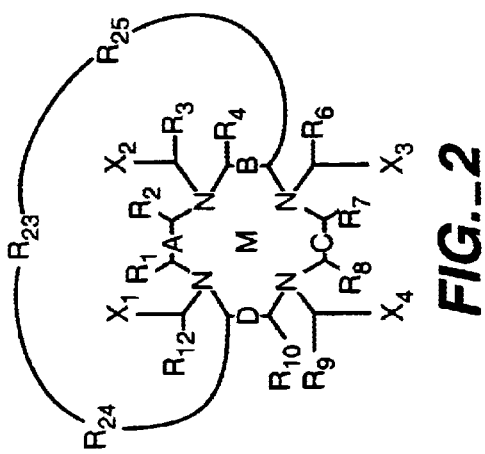
*FIG._2*
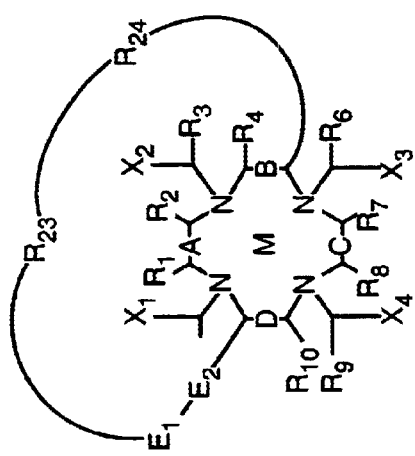
*FIG._3*

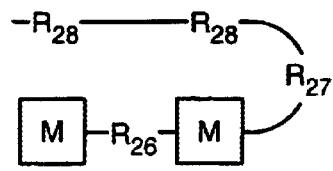
FIG._6A
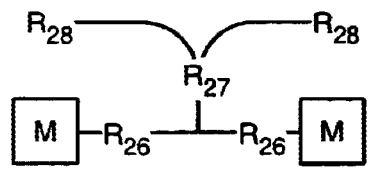
FIG._6B
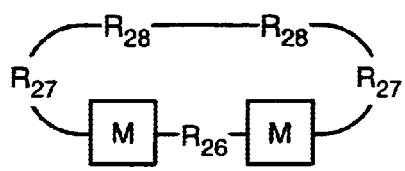
FIG._6C
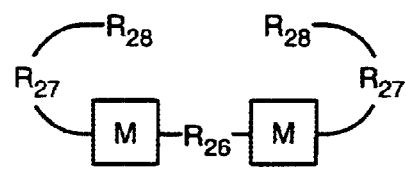
FIG._6D
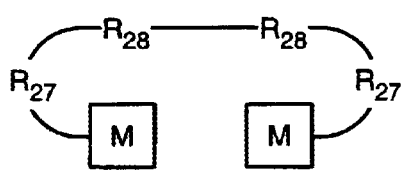
FIG._6E
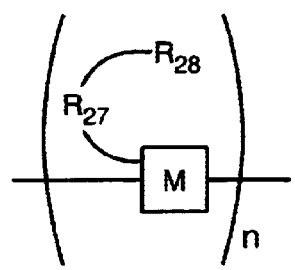
FIG._6F
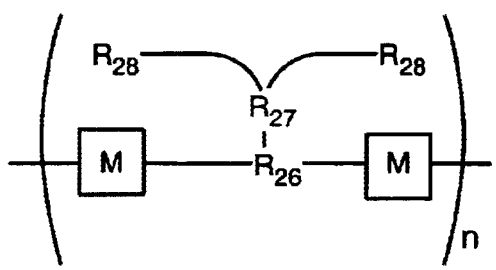
FIG._6G
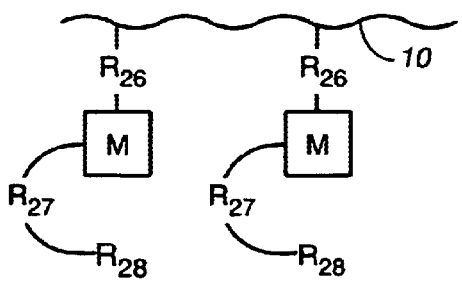
FIG._6H
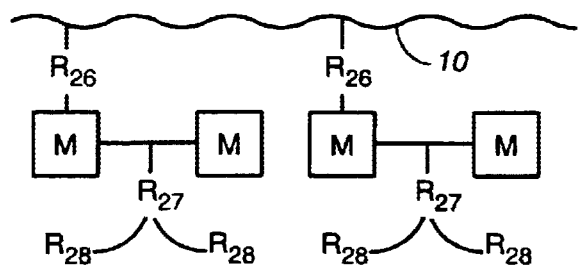
FIG._6I

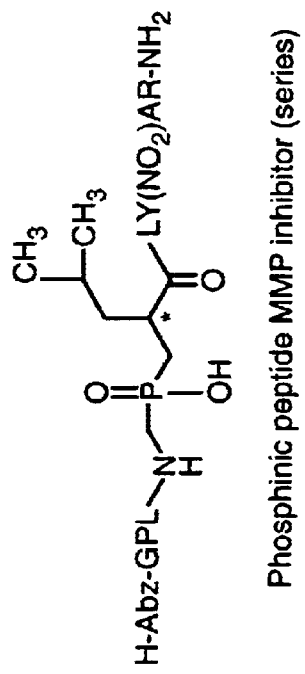
FIG._7A
GM6001
N-[2(R)-2-(hydroxamido carbonylmethyl)-
4-methylpentanoyl]-L-tryptophane methylamide
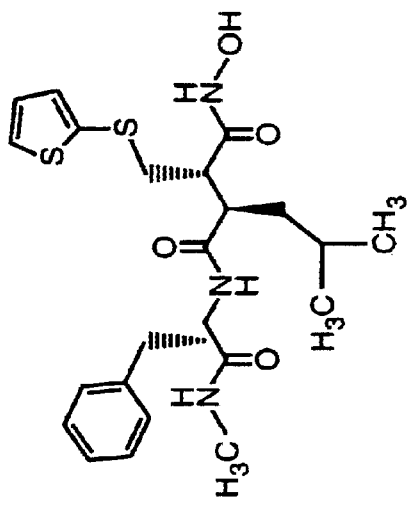
FIG._7B
Phosphinic peptide MMP inhibitor (series)
H-Abz-GPL~P~LY(NO₂)AR-NH₂
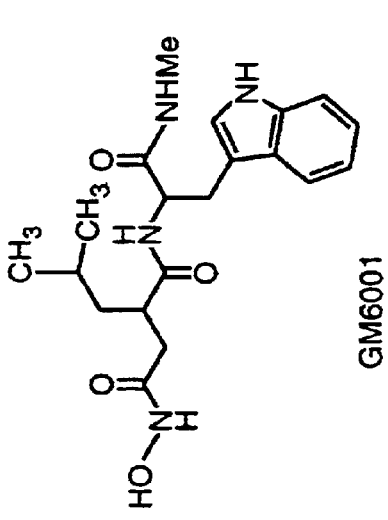
FIG._7C
Marimastat - BB-2516
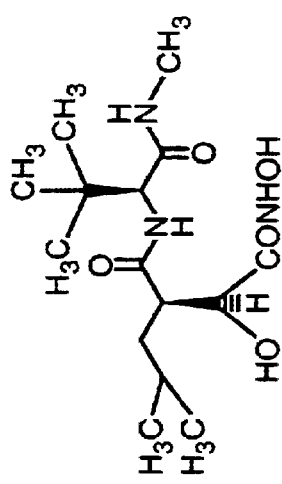
FIG._7D
Batimastat - BB94
[2R-[1(S*),2R*,3S*]]-N⁴-Hydroxy-N¹-[2-(methylamino)-2-oxo
-1-(phenylmethyl)ethyl]-2-(2-methylpropyl)-3-[(2-thienylthio)
methyl]butanediamide

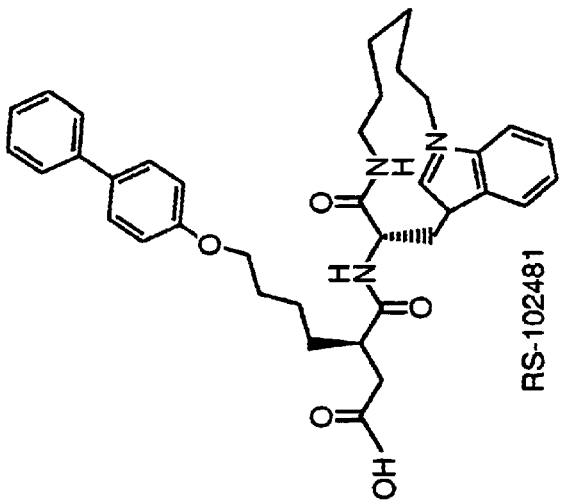
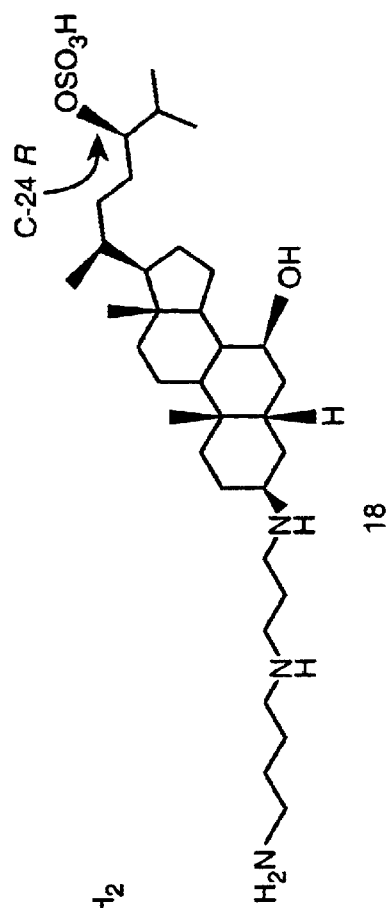
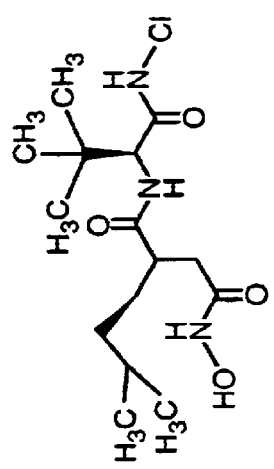
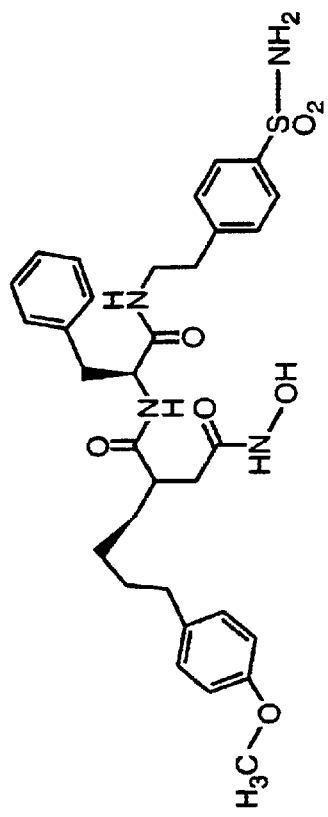
FIG. 7E  Ro31-9790
FIG. 7F  RS-102481
FIG. 7G  CT1418
FIG. 7H

FUNCTIONAL MRI AGENTS FOR CANCER IMAGING

This is a continuing application of U.S. Ser. No. 60/201,816, filed May 4, 2000.

FIELD OF THE INVENTION

The invention relates to novel magnetic resonance imaging contrast agents for imaging cancer.

BACKGROUND OF THE INVENTION

Magnetic resonance imaging (MRI) is a diagnostic and research procedure that uses high magnetic fields and radio-frequency signals to produce images. The most abundant molecular species in biological tissues is water. It is the quantum mechanical "spin" of the water proton nuclei that ultimately gives rise to the signal in all imaging experiments. In MRI the sample to be imaged is placed in a strong static magnetic field (1–12 Tesla) and the spins are excited with a pulse of radio frequency (RF) radiation to produce a net magnetization in the sample. Various magnetic field gradients and other RF pulses then act on the spins to code spatial information into the recorded signals. MRI is able to generate structural information in three dimensions in relatively short time spans.

The Image.

MR images are typically displayed on a gray scale with black the lowest and white the highest measured intensity (I). This measured intensity I=C*M, where C is the concentration of spins (in this case, water concentration) and M is a measure of the magnetization present at time of the measurement. Although variations in water concentration (C) can give rise to contrast in MR images, it is the strong dependence of the rate of change of M on local environment that is the source of image intensity variation in MRI. Two characteristic relaxation times, $T_1$ & $T_2$, govern the rate at which the magnetization can be accurately measured. $T_1$ is the exponential time constant for the spins to decay back to equilibrium after being perturbed by the RF pulse. In order to increase the signal-to-noise ratio (SNR) a typical MR imaging scan (RF & gradient pulse sequence and data acquisition) is repeated at a constant rate for a predetermined number of times and the data averaged. The signal amplitude recorded for any given scan is proportional to the number of spins that have decayed back to equilibrium since the previous scan. Thus, regions with rapidly decaying spins (i.e. short $T_1$ values) will recover all of their signal amplitude between successive scans.

The measured intensities in the final image will accurately reflect the spin density (i.e. water content). Regions with long $T_1$ values compared to the time between scans will progressively lose signal until a steady state condition is reached and will appear as darker regions in the final image. Changes in $T_2$ (spin-spin relaxation time) result in changes in the signal linewidth (shorter $T_2$ values) yielding larger linewidths. In extreme situations the linewidth can be so large that the signal is indistinguishable from background noise. In clinical imaging, water relaxation characteristics vary from tissue to tissue, providing the contrast which allows the discrimination of tissue types. Moreover, the MRI experiment can be setup so that regions of the sample with short $T_1$ values and/or long $T_2$ values are preferentially enhanced so called $T_1$-weighted and $T_2$-weighted imaging protocol.

MRI Contrast Agents.

There is a rapidly growing body of literature demonstrating the clinical effectiveness of paramagnetic contrast agents (currently 8 are in clinical trials or in use). The capacity to differentiate regions/tissues that may be magnetically similar but histologically distinct is a major impetus for the preparation of these agents. In the design of MRI agents, strict attention must be given to a variety of properties that will ultimately effect the physiological outcome apart from the ability to provide contrast enhancement. Two fundamental properties that must be considered are biocompatability and proton relaxation enhancement. Biocompatability is influenced by several factors including toxicity, stability (thermodynamic and kinetic), pharmacokinetics and biodistribution. Proton relaxation enhancement (or relaxivity) is chiefly governed by the choice of metal and rotational correlation times.

The first feature to be considered during the design stage is the selection of the metal atom, which will dominate the measured relaxivity of the complex. Paramagnetic metal ions, as a result of their unpaired electrons, act as potent relaxation enhancement agents. They decrease the $T_1$ and $T_2$ relaxation times of nearby ($r^6$ dependence) spins. Some paramagnetic ions decrease the $T_1$ without causing substantial linebroadening (e.g. gadolinium(III), ($Gd^{3+}$)), while others induce drastic linebroadening (e.g. superparamagnetic iron oxide). The mechanism of $T_1$ relaxation is generally a through space dipole-dipole interaction between the unpaired electrons of the paramagnet (the metal atom with an unpaired electron) and bulk water molecules (water molecules that are not "bound" to the metal atom) that are in fast exchange with water molecules in the metal's inner coordination sphere (are bound to the metal atom).

For example, regions associated with a $Gd^{3+}$ ion (near-by water molecules) appear bright in an MR image where the normal aqueous solution appears as dark background if the time between successive scans in the experiment is short (i.e. $T_1$ weighted image). Localized $T_2$ shortening caused by superparamagnetic particles is believed to be due to the local magnetic field inhomogeneities associated with the large magnetic moments of these particles. Regions associated with a superparamagnetic iron oxide particle appear dark in an MR image where the normal aqueous solution appears as high intensity background if the echo time (TE) in the spin-echo pulse sequence experiment is long (i.e. $T_2$-weighted image). The lanthanide atom $Gd^{3+}$ is by the far the most frequently chosen metal atom for MRI contrast agents because it has a very high magnetic moment ($U^2$=63 $BM^2$), and a symmetric electronic ground state, ($S^8$). Transition metals such as high spin Mn(II) and Fe(III) are also candidates due to their high magnetic moments.

Once the appropriate metal has been selected, a suitable ligand or chelate must be found to render the complex nontoxic. The term chelator is derived from the Greek word chele which means a "crabs claw", an appropriate description for a material that uses its many "arms" to grab and hold on to a metal atom (see DTPA below). Several factors influence the stability of chelate complexes include enthalpy and entropy effects (e.g. number, charge and basicity of coordinating groups, ligand field and conformational effects). Various molecular design features of the ligand can be directly correlated with physiological results. For example, the presence of a single methyl group on a given ligand structure can have a pronounced effect on clearance rate. While the addition of a bromine group can force a given complex from a purely extracellular role to an effective agent that collects in hepatocytes.

Diethylenetriaminepentaacetic (DTPA) chelates and thus acts to detoxify lanthanide ions. The stability constant (K) for $Gd(DTPA)^{2-}$ is very high (logK=22.4) and is more commonly known as the formation constant (the higher the logK, the more stable the complex). This thermodynamic parameter indicates the fraction of $Gd^{3+}$ ions that are in the unbound state will be quite small and should not be confused with the rate (kinetic stability) at which the loss of metal occurs ($k_f/k_d$). The water soluble $Gd(DTPA)^{2-}$ chelate is stable, nontoxic, and one of the most widely used contrast enhancement agents in experimental and clinical imaging research. It was approved for clinical use in adult patients in June of 1988. It is an extracellular agent that accumulates in tissue by perfusion dominated processes.

To date, a number of chelators have been used, including diethylenetriaminepentaacetic (DTPA), 1,4,7,10-tetraazacyclododecane'-N,N'N'',N'''-tetracetic acid (DOTA), and derivatives thereof. See U.S. Pat. Nos. 5,155,215, 5,087,440, 5,219,553, 5,188,816, 4,885,363, 5,358,704, 5,262,532, and Meyer et al., Invest. Radiol. 25: S53 (1990).

Image enhancement improvements using Gd(DTPA) are well documented in a number of applications (Runge et al., Magn, Reson. Imag. 3:85 (1991); Russell et al., AJR 152:813 (1989); Meyer et al., Invest. Radiol. 25:S53 (1990)) including visualizing blood-brain barrier disruptions caused by space occupying lesions and detection of abnormal vascularity. It has recently been applied to the functional mapping of the human visual cortex by defining regional cerebral hemodynamics (Belliveau et al., (1991) 254:719).

Another chelator used in Gd contrast agents is the macrocyclic ligand 1,4,7,10-tetraazacyclododecane-N,N',N'',N'''-tetracetic acid (DOTA). The Gd-DOTA complex has been thoroughly studied in laboratory tests involving animals and humans. The complex is conformationally rigid, has an extremely high formation constant (logk=28.5), and at physiological pH possess very slow dissociation kinetics. Recently, the GdDOTA complex was approved as an MRI contrast agent for use in adults and infants in France and has been administered to over 4500 patients.

Previous work describes a new class of MRI contrast agents that report on physiologic or metabolic an processes within a biological or other type of sample. See U.S. Pat. Nos. 5,707,605 and 5,980,862.

However, it would be desirable to have these functional MRI agents image cancerous cells or tissues. Accordingly, it is an object of the present invention to provide MRI contrast or enhancement agents which allow the visualization and detection of cancerous cells and tissues.

SUMMARY OF THE INVENTION

In accordance with the objects outlined above, the present invention providesMRI agent compositions comprising a first Gd(III) ion bound to a first chelator such that said Gd(III) ion has coordination atoms in at least 7 coordination sites of said Gd(III) ion and a first tumor associated activatable guarding moiety (TAAGM) covalently attached to the first chelator which hinders the rapid exchange of water in the remaining coordination sites of said first Gd(III) ion. The TAAGM is capable of interacting with a cancer target substance such that the exchange of water in the remaining coordination sites of the first Gd(III) ion is increased.

In an additional aspect, the present invention provides MRI agents having the formula:

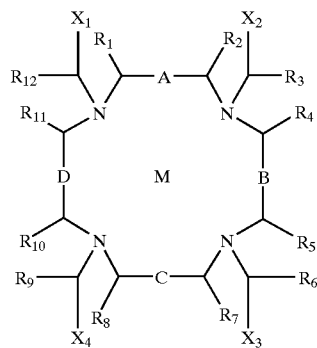

wherein

M is a paramagnetic metal ion selected from the group consisting of Gd(III), Fe(III), Mn(II), Yt(III), Cr(III) and Dy(III);

A, B, C and D are either single bonds or double bonds;

$X_1$, $X_2$, $X_3$ and $X_4$ are —OH, —COO—, —$CH_2$OH —$CH_2$COO—, or a tumor associated activatible guarding moiety (TMGM);

$R_1$–$R_{12}$ are selected from the group consisting of hydrogen, alkyl, aryl, sulfur moieties, amine groups, oxo groups, carbonyl groups, halogens, nitro groups, imino groups, alcohol groups, alkoxy groups, amido groups, phosphorus moieties, ethylene glycols, ketones, aldehydes, esters, ethers, TAAGMs and targeting moieties;

wherein at least one of $X_1$–$X_4$ and $R_1$–$R_{12}$ is a TMGM.

BRIEF DESCRIPTION OF THE DRAWINGS

FIG. 1 depicts the synthesis of a preferred cancer agent wherein the cancer target is the enzyme β-glucuronidase. Compound I is a preferred agent.

FIG. 2 depicts a preferred embodiment, In this embodiment, $R_{23}$, $R_{24}$ and $R_{25}$ comprise a TAAGM, with $R_{23}$ being a coordination site barrier which also serves to contribute a coordination atom. It is to be understood that the $R_{24}$ and $R_{25}$ groups may be attached at any of the $R_1$ to $R_{12}$ positions. Preferred $R_{23}$ groups include, but are not limited to, compounds listed above that provide a coordination atom, TAAGMs, and those shown in FIG. 4. $R_{24}$ and $R_{25}$ may also comprise a linker, as defined herein. Preferred $R_{24}$ and $R_{25}$ groups include enzyme substrates which are cleaved upon exposure to the enzyme, such as carbohydrates and peptides.

FIG. 3 depicts an alternative embodiment. In this embodiment, there may not be covalent attachment at both ends. Rather, as discussed herein, effective "tethering" of the TAAGM down over the metal ion may also be done by engineering in other non-covalent interactions that will serve to increase the affinity of the TAAGM to the chelator complex. Thus, for example, electrostatic interactions may be used. The blocking moeity/coordination site barrier occupies the $X_3$ position, although any position may be utilized. $E_1$ and $E_2$ are electrostatic moieties bearing opposite charges. In this figure, the $E_2$ group is shown at position $R_8$, although any position may be used.

FIG. 4 depicts a representative complex of the invention, where the blocking moiety is tethered at one end only. As will be appreciated, the A, B, C and D bonds are depicted as single bonds, and there may be any number of additional R groups as outlined herein. The blocking moiety comprises a linker, $R_{13}$, which is preferably an enzyme substrate, and a coordination site barrier ($R_{23}$).

FIG. 5 depicts a representative complex of the invention, wherein the blocking moiety is tethered at two ends.

FIGS. 6A, 6B, 6C, 6D, 6E, 6F, and 6G depict several of the possible conformations of the dimer embodiments. Boxes represent chelators, with M being the paramagnetic metal ions. FIGS. 6A and 6B represent two possible duplex conformations. In FIG. 6A, $R_{27}$ can be a linker, such as described herein as $R_{26}$, a cleavable moiety such as an enzyme substrate such as a peptide, or a blocking moiety that will preferentially interact with the target molecule. $R_{28}$, which may or may not be present depending on $R_{27}$, is a coordination site barrier similar to $R_{23}$ or a blocking moiety. FIG. 6B has $R_{28}$ blocking moieties or coordination site barriers attached via an $R_{27}$ group to two chelators. FIG. 6C is similar to FIG. 6A, but at least one of the $R_{27}$ groups must be a cleavable moiety. FIG. 6D depicts the case where two blocking moieties or coordination site barriers are present; if $R_{27}$ is a blocking moiety, $R_{28}$ need not be present. FIG. 6E is similar to 6B but the chelators need not be covalently attached. FIGS. 6F (single MRI agents) and 6G (duplex agents) are multimers of MRI contrast agents, wherein n can be from 1 to 1000, with from 1 to about 20 being preferred, and from about 1 to 10 being especially preferred. FIGS. 6H and 6I depict polymer 10 as defined herein being attached to either single MRI agents (6H) or duplex MRI agents (6I).

FIGS. 7A–7H depict a number of suitable TAAGMs. FIGS. 7A–7G are MMP inhibitors, and FIG. 7H is squalamine.

DETAILED DESCRIPTION OF THE INVENTION

The present invention provides novel targeted magnetic resonance imaging contrast agents which can detect target substances that are associated with cancer. Previous work has shown MRI contrast agents that are relatively inactive, or have weak relaxivity, as contrast enhancement agents in the absence of the physiological target substance, and are activated, thus altering the MR image, in the presence of the physiological target substance. See U.S. Pat. Nos. 5,707,605 and 5,980,862, both of which are expressly incorporated by reference.

Viewed simplistically, this "trigger" mechanism, whereby the contrast agent is "turned on" (i.e. increases the relaxivity) by the presence of the target substance, is based on a dynamic equilibrium that affects the rate of exchange of water molecules in one or more coordination sites of a paramagnetic metal ion contained in the MRI contrast agents of the present invention. In turn, the rate of exchange of the water molecule is determined by the presence or absence of the target substance in the surrounding environment. Thus, in the absence of the target substance, the metal ion complexes of the invention which chelate the paramagnetic ion have reduced coordination sites available which can rapidly exchange with the water molecules of the local environment. In such a situation, the water coordination sites are substantially occupied or blocked by the coordination atoms of the chelator and at least one guarding moiety. Thus, the paramagnetic ion has essentially no water molecules in its "inner-coordination sphere", i.e. actually bound to the metal when the target substance is absent. It is the interaction of the paramagnetic metal ion with the protons on the inner coordination sphere water molecules and the rapid exchange of such water molecules that cause the high observed relaxivity, and thus the imaging effect, of the paramagnetic metal ion. Accordingly, if all the coordination sites of the metal ion in the metal ion complex are occupied with moieties other than water molecules, as is the case when the target substance is absent, there is little if any net enhancement of the imaging signal by the metal ion complexes of the invention. However, when present, the target substance interacts with the guarding moiety or moieties of the metal ion complex, effectively freeing at least one of the inner-sphere coordination sites on the metal ion complex. The water molecules of the local environment are then available to occupy the inner-sphere coordination site or sites, which will cause an increase in the rate of exchange of water and relaxivity of the metal ion complex toward water thereby producing image enhancement which is a measure of the presence of the target substance.

It should be understood that even in the absence of the target substance, at any particular coordination site, there will be a dynamic equilibrium for one or more coordination sites as between a coordination atom of the guarding moiety and water molecules. That is, even when a coordination atom is tightly bound to the metal, there will be some exchange of water molecules at the site. However, in most instances, this exchange of water molecules is neither rapid nor significant, and does not result in significant image enhancement. However, upon exposure to the target substance, the guarding moiety dislodges from the coordination site and the exchange of water is increased, i.e. rapid exchange and therefore an increase in relaxivity may occur, with significant image enhancement.

Generally, a 2 to 5% change in the MRI signal used to generate the image is sufficient to be detectable. Thus, it is preferred that the agents of the invention in the presence of a target substance increase the MRI signal by at least 2 to 5% as compared to the signal gain the absence of the target substance. Signal enhancement of 2 to 90% is preferred, and 10 to 50% is more preferred for each coordination site made available by the target substance interaction with the guarding moiety. That is, when the guarding moiety occupies two or more coordination sites, the release of the guarding moiety can result in double the increase in signal or more as compared to a single coordination site.

In addition, the present invention provides for the use of targeting moieties attached to these activatable MRI agents. By utilizing a targeting moiety, defined below, such as a cancer targeting moiety, that can direct the MRI agent to a particular cell type, tissue, or location, the MRI agents of the invention become more effective, discriminatory and selective, particularly with regard to signal detection of disease pathology.

Accordingly, the complexes of the invention comprise a paramagnetic metal ion bound to a complex comprising a chelator and a cancer directed guarding moiety. By "paramagnetic metal ion", "paramagnetic ion" or "metal ion" herein is meant a metal ion which is magnetized parallel or antiparallel to a magnetic field to an extent proportional to the field. Generally, these are metal ions which have unpaired electrons; this is a term understood in the art. Examples of suitable paramagnetic metal ions, include, but are not limited to, gadolinium III (Gd+3 or Gd(III)), iron IIII (Fe+3 or Fe(III)), manganese II (Mn+2 or Mn(II)), yttrium III (Yt+3 or Yt(III)), dysprosium (Dy+3 or Dy(III)), and chromium (Cr(III) or Cr+3). In a preferred embodiment the paramagnetic ion is the lanthanide atom Gd(III), due to its high magnetic moment ($u^2$=63BM2), a symmetric electronic ground state (S8), and its current approval for diagnostic use in humans.

In addition to the metal ion, the metal ion complexes of the invention comprise a chelator and a cancer directed guarding moiety which may be covalently attached to the chelator. Due to the relatively high toxicity of many of the paramagnetic ions, the ions are rendered nontoxic in physiological systems by binding to a suitable chelator. Thus, the substitution of TAAGMs in coordination sites of the chelator, which in the presence of the cancer target are capable of vacating the coordination sites in favor of water molecules, may render the metal ion complex more toxic by decreasing the half-life of dissociation for the metal ion complex. Thus, in a preferred embodiment, only a single coordination site is occupied or blocked by a cancer directed guarding moiety. However, for some applications, e.g. analysis of tissue and the like, the toxicity of the metal ion complexes may not be of paramount importance. Similarly, some metal ion complexes are so stable that even the replacement of one or more additional coordination atoms with a cancer directed guarding moiety does not significantly effect the half-life of dissociation. For example, DOTA, described below, when complexed with Gd(III) is extremely stable. Accordingly, when DOTA serves as the chelator, several of the coordination atoms of the chelator may be replaced with TAAGMs without a significant increase in toxicity. Additionally such an agent would potentially produce a larger signal since it has two or more coordination sites which are rapidly exchanging water with the bulk solvent.

There are a variety of factors which influence the choice and stability of the chelate metal ion complex, including enthalpy and entropy effects (e.g. number, charge and basicity of coordinating groups, ligand field and conformational effects).

In general, the chelator has a number of coordination sites containing coordination atoms which bind the metal ion. The number of coordination sites, and thus the structure of the chelator, depends on the metal ion. The chelators used in the metal ion complexes of the present invention preferably have at least one less coordination atom (n−1) than the metal ion is capable of binding (n), since at least one coordination site of the metal ion complex is occupied or blocked by a blocking moeity, as described below, to confer functionality on the metal ion complex. Thus, for example, Gd(III) may have 8 strongly associated coordination atoms or ligands and is capable of weakly binding a ninth ligand. Accordingly, suitable chelators for Gd(III) will have less than 9 coordination atoms. In a preferred embodiment, a Gd(III) chelator will have 8 coordination atoms, with a cancer directed guarding moiety either occupying or blocking the remaining site in the metal ion complex. In an alternative embodiment, the chelators used in the metal ion complexes of the invention have two less coordination atoms (n−2) than the metal ion is capable of binding (n), with these coordination sites occupied by one or more TAAGMs. Thus, alternative embodiments utilize Gd(III) chelators with at least 5 coordination atoms, with at least 6 coordination atoms being preferred, at least 7 being particularly preferred, and at least 8 being especially preferred, with the cancer directed guarding moiety either occupying or blocking the remaining sites. It should be appreciated that the exact structure of the chelator and cancer directed guarding moiety may be difficult to determine, and thus the exact number of coordination atoms may be unclear. For example, it is possible that the chelator provide a fractional or non-integer number of coordination atoms; i.e. the chelator may provide 7.5 coordination atoms, i.e. the 8th coordination atom is on average not fully bound to the metal ion. However, the metal ion complex may still be functional, if the 8th coordination atom is sufficiently bound to prevent the rapid exchange of water at the site, and/or the cancer directed guarding moiety impedes the rapid exchange of water at the site.

There are a large number of known macrocyclic chelators or ligands which are used to chelate lanthanide and paramagnetic ions. See for example, Alexander, Chem. Rev. 95:273–342 (1995) and Jackels, Pharm. Med. Imag, Section III, Chap. 20, p645 (1990), expressly incorporated herein by reference, which describes a large number of macrocyclic chelators and their synthesis. Similarly, there are a number of patents which describe suitable chelators for use in the invention, including U.S. Pat. Nos. 5,155,215, 5,087,440, 5,219,553, 5,188,816, 4,885,363, 5,358,704, 5,262,532, and Meyer et al., Invest. Radiol. 25: S53 (1990), all of which are also expressly incorporated by reference. Thus, as will be understood by those in the art, any of the known paramagnetic metal ion chelators or lanthanide chelators can be easily modified using the teachings herein to further comprise at least one cancer directed guarding moiety.

A preferred chelator, particularly when the metal ion is Gd(III), is 1,4,7,10-tetraazacyclododecane-N,N',N", N'''-tetracetic acid (DOTA) or substituted DOTA. DOTA has the structure shown below:

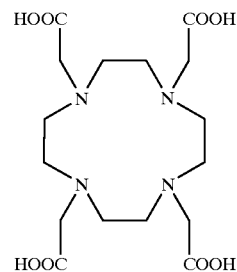

By "substituted DOTA" herein is meant that the DOTA may be substituted at any of the following positions, as shown below:

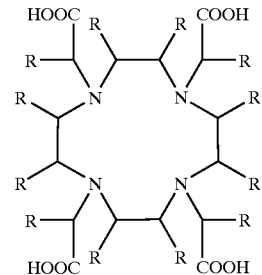

As will be appreciated by those in the art, a wide variety of possible R substituent groups may be used. Suitable R substitution groups, for this and other structures of the invention, include, but are not limited to, hydrogen, alkyl groups including substituted alkyl groups and heteroalkyl groups as defined below, aryl groups including substituted aryl and heteroaryl groups as defined below, sulfur moieties, amine groups, oxo groups, carbonyl groups, halogens, nitro groups, imino groups, alcohol groups, alkyoxy groups, amido groups, phosphorus moieties, ethylene glycols, ketones, aldehydes, esters, ethers, TAAGMs and targeting moieties. In addition, suitable substitution groups include substitution groups disclosed for DOTA and DOTA-type compounds in U.S. Pat. Nos. 5,262,532, 4,885,363, and 5,358,704 and WO 98/05625.

In addition, R groups on adjacent carbons, or adjacent R groups, can be attached to form cycloalkyl or cycloaryl groups, including heterocycloalkyl and heterocycloaryl groups together with the carbon atoms of the chelator, such as is described below and in U.S. Pat. No. 5,358,704, expressly incorporated by reference. These ring structures may be similarly substituted at any position with R groups.

In addition, as will be appreciated by those skilled in the art, each position designated above may have two R groups attached (R'and R"), although in a preferred embodiment only a single non-hydrogen R group is attached at any particular position; that is, preferably at least one of the R groups at each position is hydrogen. Thus, if R is an alkyl or aryl group, there is generally an additional hydrogen attached to the carbon, although not depicted herein. In a preferred embodiment, one R group is a cancer directed guarding moiety and the other R groups are hydrogen; that is, it is preferred to have only two hydrogens at each R position except for the positions occupied by the cancer directed guarding moiety and the targeting moiety. Similarly, preferred embodiments utilize one R group as a targeting moiety and the other R groups (except for the cancer directed guarding moiety position) as hydrogen.

By "alkyi group" or grammatical equivalents herein is meant a straight or branched chain alkyl group, with straight chain alkyl groups being preferred. If branched, it may be branched at one or more positions, and unless specified, at any position. The alkyl group may range from about 1 to about 30 carbon atoms (C1–C30), with a preferred embodiment utilizing from about 1 to about 20 carbon atoms (C1–C20), with about C1 through about C12 to about C15 being preferred, and C1 to C5 being particularly preferred, although in some embodiments the alkyl group may be much larger. Also included within the definition of an alkyl group are cycloalkyl groups such as C5 and C6 rings, and heterocyclic rings with nitrogen, oxygen, sulfur or phosphorus. Alkyl also includes heteroalkyl, with heteroatoms of sulfur, oxygen, nitrogen, and silicone being preferred. Alkyl includes substituted alkyl groups. By "substituted alkyl group" herein is meant an alkyl group further comprising one or more substitution moieties "R", as defined above.

A preferred heteroalkyl group is an alkyl amine. By "alkyl amine" or grammatical equivalents herein is meant an alkyl group as defined above, substituted with an amine group at any position. In addition, the alkyl amine may have other substitution groups, as outlined above for alkyl group. The amine may be primary (—$NH_2R$), secondary (—$NHR_2$), or tertiary (—$NR_3$). When the amine is a secondary or tertiary amine, suitable R groups are alkyl groups as defined above. A preferred alkyl amine is p-aminobenzyl. When the alkyl amine serves as the coordination site barrier, as described below, preferred embodiments utilize the nitrogen atom of the amine as a coordination atom, for example when the alkyl amine includes a pyridine or pyrrole ring.

By "aryl group" or "aromatic group" or grammatical equivalents herein is meant an aromatic monocyclic or polycyclic hydrocarbon moiety generally containing 5 to 14 carbon atoms (although larger polycyclic rings structures may be made) and any carbocylic ketone or thioketone derivative thereof, wherein the carbon atom with the free valence is a member of an aromatic ring. Aromatic groups include arylene groups and aromatic groups with more than two atoms removed. For the purposes of this application aromatic includes heterocycle. "Heterocycle" or "heteroaryl" means an aromatic group wherein 1 to 5 of the indicated carbon atoms are replaced by a heteroatom chosen from nitrogen, oxygen, sulfur, phosphorus, boron and silicon wherein the atom with the free valence is a member of an aromatic ring, and any heterocyclic ketone and thioketone derivative thereof. Thus, heterocycle includes thienyl, furyl, pyrrolyl, pyrimidinyl, oxalyl, indolyl, purinyl, quinolyl, isoquinolyl, thiazolyl, imidozyl, etc. As for alkyl groups, the aryl group may be substituted with a substitution group, generally depicted herein as R.

It should also be noted that neighboring carbon atoms of the chelate may be joined together to form cycloalkyl or aryl groups, which may be substituted as outlined herein.

By "amino groups" or grammatical equivalents herein is meant —$NH_2$ (amine groups), —NHR and —$NR_2$ groups, with R being as defined herein.

By "nitro group" herein is meant an —$NO_2$ group.

By "sulfur containing moieties" herein is meant compounds containing sulfur atoms, including but not limited to, thia-, thio- and sulfo-compounds (including sulfones ($SO_2$) and sulfides (SO)), thiols (—SH and —SR), and sulfides (—RSR—).

By "phosphorus containing moieties" herein is meant compounds containing phosphorus, including, but not limited to, phosphines, phosphites and phosphates. A preferred phosphorous moiety is the —PO(OH)(R)$_2$ group. The phosphorus may be an alkyl phosphorus; for example, DOTEP utilizes ethylphosphorus as a substitution group on DOTA. A preferred embodiment has a —PO(OH)$_2R_{25}$ group, with $R_{25}$ being a substitution group as outlined herein.

By "silicon containing moieties" herein is meant compounds containing silicon.

By "ketone" herein is meant an —RCOR— group.

By "aldehyde" herein is meant an —RCOH group.

By "ether" herein is meant an —R—O—R group.

By "alkyoxy group" herein is meant an —OR group.

By "ester" herein is meant a —COOR group.

By "halogen" herein is meant bromine, iodine, chlorine, or fluorine. Preferred substituted alkyls are partially or fully halogenated alkyls such as $CF_3$, etc.

By "alcohol" herein is meant —OH groups, and alkyl alcohols —ROH.

By "amido" herein is meant —RCONH— or RCONR— groups.

By "ethylene glycol" or "(poly)ethylene glycol" herein is meant a —(O—$CH_2$—$CH_2$)$_n$— group, although each carbon atom of the ethylene group may also be singly or doubly substituted, i.e. —(O—$CR_2$—$CR_2$)$_n$—, with R as described above. Ethylene glycol derivatives with other heteroatoms in place of oxygen (i.e. —(N—$CH_2$—$CH_2$)$_n$— or —(S—$CH_2$—$CH_2$)$_n$—, or with substitution groups) are also preferred.

Preferred substitution groups include, but are not limited to, alkyl, alkyoxy, amide, hydrogen, aryl and targeting moeities.

The substitution group may also be a targeting moiety or a cancer directed guarding moiety, as is described below.

In an alternative embodiment, a preferred chelator, particularly when the metal ion is Gd(III), is diethylenetriaminepentaacetic acid (DTPA) or substituted DTPA. DPTA has the structure shown below:

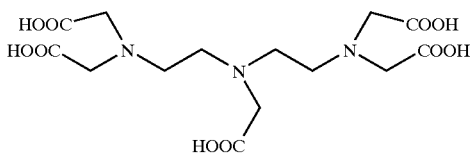

By "substituted DPTA" herein is meant that the DPTA may be substituted at any of the following positions, as shown below:

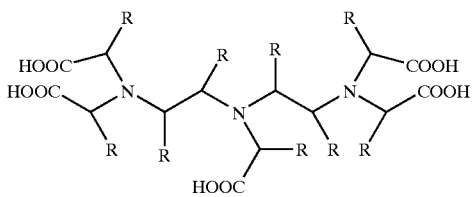

See for example U.S. Pat. No. 5,087,440.

Suitable R substitution groups include those outlined above for DOTA. Again, those skilled in the art will appreciate that there may be two R groups (R' and R") at each position designated above, although as described herein, at least one of the groups at each position is hydrogen, which is generally not depicted herein. In addition, adjacent R groups may be joined to form cycloalkyl or -aryl structures.

In an alternative embodiment, when the metal ion is Gd(III), a preferred chelator is 1,4,7,10-tetraazacyclododecane-N,N',N",N'''-tetraethylphosphorus (DOTEP) or substituted DOTEP (see U.S. Pat. No. 5,188,816). DOTEP has the structure shown below:

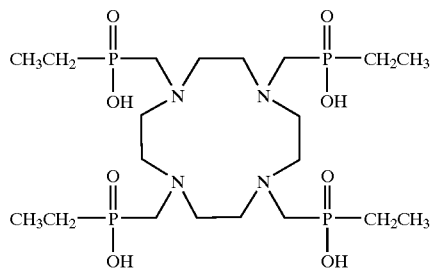

DOTEP may have similar R substitution groups as outlined above.

Other suitable Gd(III) chelators are described in Alexander, supra, Jackels, supra, U.S. Pat. Nos. 5,155,215, 5,087,440, 5,219,553, 5,188,816, 4,885,363, 5,358,704, 5,262,532, and Meyer et al., Invest. Radiol. 25: S53 (1990), among others.

When the paramagnetic ion is Fe(III), appropriate chelators will have less than 6 coordination atoms, since Fe(III) is capable of binding 6 coordination atoms. Suitable chelators for Fe(III) ions are well known in the art, see for example Lauffer et al., J. Am. Chem. Soc. 109:1622 (1987); Lauffer, Chem. Rev. 87:901–927 (1987); and U.S. Pat. Nos. 4,885,363, 5,358,704, and 5,262,532, all which describe chelators suitable for Fe(III).

When the paramagnetic ion is Mn(II) (Mn+2), appropriate chelators will have less than 5 or 6 coordination atoms, since Mn(II) is capable of binding 6 or 7 coordination atoms. Suitable chelators for Mn(II) ions are well known in the art; see for example Lauffer, Chem. Rev. 87:901–927 (1987) and U.S. Pat. Nos. 4,885,363, 5,358,704, and 5,262,532.

When the paramagnetic ion is Yt(III), appropriate chelators will have less than 7 or 8 coordination atoms, since Yt(III) is capable of binding 8 or 9 coordination atoms. Suitable chelators for Yt(III) ions include, but are not limited to, DOTA and DPTA and derivatives thereof (see Moi et al., J. Am. Chem. Soc. 110:6266–6267 (1988)) and those chelators described in U.S. Pat. No. 4,885,363 and others, as outlined above.

When the paramagnetic ion is Dy+3 (Dy(III)), appropriate chelators will have less than 7 or 8 coordination atoms, since DyIII is capable of binding 8 or 9 coordination atoms. Suitable chelators are known in the art, as above.

In a preferred embodiment, as is further described below, the chelator and the tumor associated activable guarding moiety ("TAAGM") are covalently linked; that is, the TAAGM is a substitution group on the chelator. In this embodiment, the substituted chelator, with the bound metal ion, comprises the metal ion complex which in the absence of the cancer target substance has all possible coordination sites occupied or blocked; i.e. it is coordinatively saturated.

In an alternative embodiment, the chelator and the TAAGM are not covalently attached. In this embodiment, the TAAGM has sufficient affinity for the metal ion to prevent the rapid exchange of water molecules in the absence of the cancer target substance. However, in this embodiment the TAAGM has a higher affinity for the cancer target substance than for the metal ion. Accordingly, in the presence of the cancer target substance, the TAAGM will have a tendency to be dislodged from the metal ion to interact with the cancer target substance, thus freeing up a coordination site in the metal ion complex and allowing the rapid exchange of water and an increase in relaxivity.

What is important is that the metal ion complex, comprising the metal ion, the chelator and the TAAGM, is not readily able to rapidly exchange water molecules when the blocking moieties are in the inner coordination sphere of the metal ion, such that in the absence of the cancer target substance, there is less or little substantial image enhancement.

In addition to the metal ions and chelators described herein, the MRI agents of the invention comprise a tumor associated activatible guarding moiety ("TAAGM"). By "guarding moiety" or "blocking moiety" or grammatical equivalents herein is meant a functional group associated with the chelator metal ion complexes of the invention which is capable of interacting with a cancer target substance and which is capable, under certain circumstances, of substantially blocking the exchange of water in at least one inner coordination site of the metal ion of the metal ion complex. For example, when bound to or associated with the metal ion complexes of the invention, the guarding moiety occupies or blocks at least one coordination site of the metal ion in the absence of the cancer target substance. Thus, the metal ion is coordinately saturated with the chelator and the guarding moiety or moieties in the absence of the cancer target substance.

The guarding moieties of the invention are cancer directed. By "tumor associated activatible guarding moiety" or "TAAGM" or "cancer directed guarding moiety" herein is meant a guarding moiety that is preferentially activated in cancerous cells or tissues. By "preferentially activated" herein is meant that the agents are not activated to a significant degree by non-pathological cells or tissues, such that a distinguishable image may be observed. It should be understood that many of the guarding moieties herein may be present in cells or tissues other than cancerous ones;

however, there is a detectable increase In the signal or image as between cancerous tissues and non-cancerous ones. In a preferred embodiment, the agent is partitioned to the location of the disease; that is, the ratio of cancerous:non-cancerous tissue image is greater than 1:1.

Thus, a cancer directed MRI agent is one that allows the imaging of cancerous cells or tissues. Suitable cancers for imaging using the compositions of the present invention include, but are not limited to, melanoma, myeloid leukemia, carcinomas of the lung, breast, ovaries, colon, kidney, bladder, liver, prostate, brain, pancreas, cervix and testes. In addition, molecules associated with angiogenesis are included.

A TAAGM may comprise several components. The TAAGM has a functional moiety which is capable of interacting with a cancer target substance, as outlined below. This functional moiety may or may not provide the coordination atom(s) of the TAAGM. In addition, TAAGMs may comprise one or more linker groups to allow for correct spacing and attachment of the components of the TAAGM. Furthermore, in the embodiment where the functional group of the TAAGM does not contribute a coordination atom, the TAAGM may comprise a coordination site barrier, which serves to either provide a coordination site atom or sterically prevent the rapid exchange of water at the coordination site; i.e. the coordination site barrier may either occupy or block the coordination site.

By "capable of interacting with a cancer cancer target substance" herein is meant that the TAAGM has an affinity for the cancer target substance, such that the TAAGM will stop blocking or occupying at least one coordination site of the metal ion complex when the cancer target substance is present. Thus, as outlined above, the TAAGM is blocking or occupying at least one coordination site of the metal ion in the absence of the cancer target substance. However, in the presence of the cancer target substance, the TAAGM associates or interacts with the cancer target substance and is released from its association with the metal ion, thus freeing at least one coordination site of the metal ion such that the rapid exchange of water can occur at this site, resulting in image enhancement.

The nature of the interaction between the TAAGM and the cancer target will depend on the cancer target to be detected or visualized via MRI. "Cancer targets" are those that are preferentially expressed or synthesized in cancer cells, tissues and/or tumors. For example, suitable cancer target substances include, but are not limited to, enzymes and proteins (including peptides) such as cell surface receptors; nucleic acids; lipids and phospholipids.

In some embodiments, the nature of the interaction is irreversible, such that the TAAGM does not reassociate to block or occupy the coordination site; for example, when the TAAGM comprises an enzyme substrate which is cleaved upon exposure to the cancer target enzyme. Alternatively, the nature of the interaction is reversible, such that the TAAGM will reassociate with the complex to hinder the exchange of water; for example, when the TAAGM comprises a receptor ligand, as outlined below.

The corresponding TAAGMs will be enzyme substrates or inhibitors, receptor ligands, antibodies, antigens, substantially complementary nucleic acids, nucleic acid binding proteins, etc.

In a preferred embodiment, the cancer target is an enzyme. In general, in this embodiment, there are two different mechanisms that can be exploited in the present invention. In a first embodiment, the guarding moiety is a substrate for the enzyme, and thus in the presence of the cancer target, the guarding moiety is cleaved off and the MRI agent is activated. In a second embodiment, the guarding moiety is an inhibitor of the cancer target enzyme. In this embodiment, upon exposure of the cancer MRI agent to the cancer target, the guarding moiety interacts with the cancer target, activating the MRI agent and simultaneously inhibiting the cancer target. Thus, both diagnosis (imaging) and treatment occurs simultaneously. In general, in the case of inhibitors, the guarding moiety is not cleaved from the MRI agent; rather, its position in the agent is altered, such that an increase in the rate of water exchange in a coordination site is increased.

In a preferred embodiment, the cancer target substance is an enzyme, and the TAAGM is an enzyme substrate. In this embodiment, the TAAGM is cleaved from the metal ion complex of the invention, allowing the exchange of water in at least one coordination site of the metal ion complex. This embodiment allows the amplification of the image enhancement since a single molecule of the cancer target substance is able to generate many activated metal ion complexes, i.e. metal ion complexes in which the TAAGM is no longer occupying or blocking a coordination site of the metal ion.

As will be appreciated by those skilled in the art, the possible enzyme cancer target substances are quite broad. The cancer target substance enzyme may be chosen on the basis of a correlation to a disease condition, for example, for diagnositic purposes. Alternatively, the metal ion complexes of the present invention may be used to establish such correlations.

Suitable classes of enzymes include, but are not limited to, hydrolases such as proteases, carbohydrases, lipases and nucleases; isomerases such as racemases, epimerases, tautomerases, or mutases; transferases, kinases and phophatases.

Many of the structures described herein as suitable for the TAAGM comprise a number of functional groups that may be used to add the TAAGM to the chelator as generally described herein, similar to the methods described for the attachment of chelators together or with other moieties. For example, using substitution groups that serve as functional groups for chemical attachment on the chelator, attachment to the functional groups (either inherent on the TAAGM or added chemically) may be accomplished. For example, for proteinaceous TAAGMs, functional groups of the amino acid side chains may be used, or the amino- or carboxyl-termini. Again, as outlined herein for other attachments, this may be done directly or through the use of linkers.

In a preferred embodiment, the TAAGM is a substrate or inhibitor for cathepsin B. The cathepsins belong to the papain superfamily of cysteine proteases. Cysteine or thiol proteases contain a cysteine residue, as well as a histidine and an asparagine, at the active site responsible for proteolysis. This superfamily also has a glutamine at the oxyanion hole.

Cathepsin B is implicated in tumor invasion and progression. Cathepsin B secretion from cells may be induced by an acidic pH of the medium, although it is functional at physiological pH. It is a protein in the extracellular matrix (ECM) degrading protease cascade and undergoes autodegradation in the absence of a substrate. Cathepsin B has been implicated in breast, cervix, ovary, stomach, lung, brain, colorectal, prostate and thyroid tumors. It is active at the local invasive stage, with stage IV tumors exhibiting significantly higher concentrations than lower staged tumors. It has been shown to be active at the tumor cell surface, at focal adhesions and invadopodia where the tumor cells contact the basal membrane and ECM. It degrades the ECM, both intracellularly and extracellularly, and includes laminin, fibronectin and collagen IV as its natural substrates. Suitable additional and synthetic substrates for use in the invention include, but are not limited to, edestin, gelatin, azo-casein, Benzyloxycarbonylarginylarginine 4-methylcoumarin-7-ylamine (Z-Arg-Arg-NH-Mec); trypsinogen; Benzyloxycarbonylphenylarginine 4-methylcoumarin-7-ylamine (Z-Phe-Arg-NH-Mec); N-α-benzyloxycarbonyl-L-arginyl-L-arginine 2-naphthylamide (Z-Arg-Arg-NNap); seffin A; Benzyloxycarbonylarginylarginine p-nitroanilide (Z-Arg-Arg-p-NA); oxidized β chian of insulin; Benzyloxycarbonylphenylarginine p-nitroanilide (Z-Phe-Arg-p-NA); α-N-benzoyl-L-arginine amide (BAA); α-N-benzoyl-L-arginine ethyl ester (BAEE); α-N-benzoyl-D,L-arginine 2-napthylamide (BANA); α-N-benzoyl-D,L-arginine p-nitroanilide (BAPA); α-N-benzoyl-L-lysine amide (BLA); α-N-benzyloxycarbonyl glycine p-nitrophenyl ester (CGN); and α-N-benzyloxycarbonyl-L-lysine p-nitrophenyl ester (CLN). See Buck et al., Biochem. J. 282 (Pt 1), 273–278 (1992); Moin et al., Biochem. J. 285 (Pt 2), 427–434 (1992); Hasnain et al., Biol. Chem. Hoppe Seyler 373, 413–418 (1992); Willenbrock et al., Biochem. J. 227, 521–528 (1985); Otto, K. in Tissue Proteinases (Barrett, A. J. and Dingle, J. T., eds.) p. 1, North-Holland, Amsterdam; Bajkowski et al. Anal. Biochem 68, 119–127 (1975) and references therein, all of which are expressly incorporated by reference.

As for all the substrates and inhibitors outlined herein, as will be appreciated by those in the art, many of the protecting groups and/or chromogenic or fluorogenic leaving groups can be altered or deleted when these molecules are used as TAAGMs and/or targeting moieties.

In addition, there are a wide variety of known inhibitors, such as cystatin C, 1-(L-trans-epoxysuccinylleucylamino)-4-guanidinobutane (also called E-64 or (N-[N-(L-3-trans-carboxyoxiran-2-carbonyl)-L-leucyl]-agmatine). See Yan et al., (1998) Biol. Chem. 379:113; Keppler et al., (1994); Biochem. Soc. Trans. 22:43; Hughes et al., PNAS USA 95:12410 (1998); Abdollahi et al., J. Soc. Gynecol. Invest. 6:32 (1999), Varughese et al., Biochemistry 31, 5172–5176 (1992); Hasnain et al, J. Biol. Chem. 267, 4713–4721 (1992), all of which are expressly incorporated by reference.

As will be appreciated by those in the art and discussed below, there are a wide variety of methods to attach these compounds to the chelates of the invention.

In a preferred embodiment, the TAAGM is a substrate or inhibitor for for cathepsin D. Cathepsin D is a 48 kDa aspartyl endoprotease with a classic Asp-Thr-Gly active site. Similar to a variety of other cathepsins, it is made as a 52 kDa precursor, procathepsin D. It is ubiquitously distributed in lysosomes. Cathepsin D has been implicated in breast, renal cell, ovary and melanoma cancers, and appears to be involved in the growth of micrometastases into clinical metastases. In tumor cells, cathepsin D is secreted into the surrounding medium resulting in delivery to the plasma membrane. Similar to cathepsin B, cathepsin D is part of the ECM degrading cascade of proteases. In addition, cathepsin D requires an acidic pH (4.5–5.0) for optimal activity. See Rochefort et al., APMIS 107:86 (1999); Xing et al., Mol. Endo. 12(9): 1310 (1998); Yazlovitskaya et al., Proc. Am. Assoc. Cancer Res. 37:#3553 519 (1996); all of which are expressly incorporated by reference.

Known cathepsin D substrates and inhibitors include, but are not limited to, substrates: gp-120 and naphthazarin (5,8-dihydroxyl-1,4-naphthoquinone) and inhibitors: pepstatine and equistatin. See Ollinger, Archives of Biochemistry & Biophysics. 373(2):346–51, 2000; El Messaoudi et al., Journal of Virology. 74(2):1004–7, 2000; Bessodes et al., Biochemical Pharmacology. 58(2):329–33, Lenarcic et al., Journal of Biological Chemistry. 274(2):563–6, 1999, all of which are expressly incorporated by reference.

In a preferred embodiment, the TAAGM is a substrate or inhibitor for cathepsin K. Cathepsin K is also an elastolytic cysteine protease, and is considered to be the most potent mammalian elastase, and also has collagenolytic activity. Cat K is considered unique among mammalian proteinases in that its collagenolytic activity does not depend on the destabilization of the triple helix of collagen in contrast to other cysteine proteases and tht it cleaves native molecules at more sites than does interstitial collagenase. Thus, cat K can degrade completely the insoluble collagen of adult cortical bone in the absence of other proteases. It is highly expressed in osteoclasts. It plays an important role in bone resorption and is essential for normal bone growth and remodeling. It has been implicated in osteoporosis, pycnodysotosis, bone cancer as well as breast cancer. It is interesting to note that breast cancer commonly metastasizes to bone, and cat K was initially identified as related to breast cancer by its presence in breast cancer cells that had spread to and invaded bone. Its substrates include, but are not limited to, elastin and collagen, and its inhibitors include, but are not limited to, Cbz-Gly-Arg-AMC; Cbz-Arg-Arg-AMC; Cbz-Gly-Gly-Arg-AMC; Cbz-Ala-Lys-Arg-AMC; Cbz-Ala-Arg-Arg-AMC; Cbz-d-Phe-Arg-AMC; Boc-Leu-Gly-Arg-AMC; H-Gly-Arg-AMC; H-Ala-Arg-AMC; Cbz-Leu-Leu-Leu-AMC; Cbz-Leu-Leu-AMC; Cbz-Phe-Gly-AMC; Cbz-Gly-Gly-Leu-AMC; Suc-Ala-Ala-Val-AMC; Cbz-Gly-Ala-Met-AMC; E-64; Leupeptin (Ac-Leu-Leu-Arg-CHO); N-acetyl-Leu-Leu-methional; Ac-Leu-Leu-Met-CHO; Ac-Leu-Val-Lys-CHO; Ac-Leu-Leu-Nle-CHO; Cbz-Lys-Leu-Leu-CHO; Cbz-Leu-Leu-Leu-CHO; Cbz-Arg-Leu-Leu-CHO; Series of 1,3-bis(acylamino)-2-propanones; series of 1,3 diamino ketones; and a series of 1,5-diacylcarbohydrazides. Suitable cathepsin K substrates include, but are not limited to, Cbz-Leu-Arg-AMC; Cbz-Val-Arg-AMC; Cbz-Phe-Arg-AMC; Cbz-Leu-Leu-Arg-AMC; Tos-Gly-Pro-Arg-AMC; Bz-; Phe-Val-Arg-AMC; H-Pro-Phe-Arg-AMC; Cbz-Val-Val-Arg-AMC; Boc-Val-Pro-Arg-AMC; Cbz-Glu-Arg-AMC; Bz-Arg-AMC; Ac-Phe-Arg-AMC; Boc-Val-Leu-Lys-AMC; Suc-Leu-Tyr-AMC; Boc-Ala-Gly-Pro-Arg-AMC; Cbz-Gly-Pro-Arg-AMC; Z-Leu-Arg-4-methoxy-b-naphthylamide (where Cbz=benzyloxycarbonyl and AMC=aminomethylcoumarin); diaminopropanones, diacylhydrazine and cystatin C. See Bossard, M. J. et al., J. Biol. Chem. 271, 12517–12524 (1996); Aibe, K. et al., Biol. Pharm. Bull. 19, 1026–1031 (1996); Votta, B. J. et al. J. Bone Miner. Res. 12, 1396–1406 (1997); Yamshita, D. S. et al. J. Am. Chem. Soc. 119, 11351–11352 (1997); DesJarlais, R. L. et al. J. Am. Chem. Soc. 120, 9114–9115 (1998); Marquis,R. W. et al. J. Med. Chem. 41, 3563–3567 (1998); Thompson et al., J. Med. Chem. 41, 3923–3927 (1998); Thompson et al., Bioorg. Med. Chem. 7, 599–605 (1999); Kamiya,T. et al. J. Biochem. (Tokyo) 123, 752–759 (1998), Shi et al,. J. Clin. Invest. 1–5 104:1191 (1999); and Sukhova et al., J. Clin. Invest. 102:576 (1998), all of which are expressly incorporated by reference.

In a preferred embodiment, the TAAGM is a substrate or inhibitor for β-glucuronidase. β-glucuronidase has been implicated in breast, colorectal and small cell lung carcinomas. β-glucuronidase hydrolyzes the glucuronide bond at the non-reducing termini of glycosamino-carbohydrates. A variety of substrates are cleaved by β-glucuronidase, including, but not limited to, phenolphthalein glucuronide, 5-bromo-4-chloro-3-indolyl-β-glucuronide, etc.

The concentration of β-glucuronidase has been shown to be low in well differentiated cell lines and high in poorly differentiated (carcinoma) cell lines. In addition, β-glucuronidase activity has been detected in stromal cells which penetrate tumors and in necrotic areas of solid tumors, where it is liberated by host inflammatory components, mainly by monocytes and granulocytes. The enzyme from cancerous tissue has been shown to be phosphorylated on carbohydrates and proteins at serine and threonine positions. β-glucuronidase is an exoglycosidase that is a homotetramer of 332 kDa. It is transported to the lysosome by the man-6-P/IGFII receptor where it is released by the acidic medium. See Feng et al., Chin. Med. J. 112(9):854 (1999); Fujita et al., GANN 75:598 (19840; Minton et al., Br. Canc. Res. Treat. 8:217 (1986); Pearson et al., Cancer 64:911 (1989); Bosslet et al., Canc. Res. 58:1195 (1998); Jain et al., Nat. Struc. Bio. 3:375 (1998); Ono et al., J. Biol. Chem. 263:5884 (1988), all of which are expressly incorporated herein by reference.

A particularly preferred embodiment is depicted as Structure 1 in FIG. 1, which also depicts the synthesis of Structure 1.

In a preferred embodiment, the TAAGM is a substrate or inhibitor for heparanase. Heparanase has been implicated in breast, bladder, prostate, colon, hepatocellular and cervix carcinomas, metastatic melanoma, neuroblastoma, mesothelioma and endothelioma. It is an endoglucuronidase (sometimes referred to as a proteoglycanase) of 50 kDA, with an inactive 65 kDa form. It is secreted by highly metastatic tumor cells, activated T-lymphocytes, mast cells, platelets and neutrophils, and appears to be involved in invasion and metastasis of tumor cells. The expression of heparanase has been correlated with the metastatic potential of lymphoma, fibrosarcoma and melanoma cell lines, and has been detected in the urine of tumor-bearing patients. Its substate is heparan sulfate proteoglycans which are essential in the self-assembly and insolubility of the extracellular matrix. There are a variety of known inhibitors, including heparin and other anti-coagulant molecules of polysulfated polysaccharides such as phosphomanno-pentose sulfate. See Vlodasvsky et al., Nature Med. 5:793 (1999); Hulett et al., Nature Med. 5:803 (1999), both of which are incorporated by reference.

In a preferred embodiment, the TAAGM is a substrate or inhibitor for hepsin. Hepsin has been implicated in ovarian cancer, and appears to be involved in tumor invasion and metastasis by allowing implantation and invasion of neighboring cells. It is a serine protease with a classic catalytic triad (ser-his-asn), and may activate matrix metalloproteinases (MMP). It degrades the ECM through peptide bond cleavage, and is found extracellularly. See Tantimoto et al., Proc. Am. Assoc. Cancer Res. 38:(#2765):413 (1997).

In a preferred embodiment, the TAAGM is a substrate or inhibitor for a matrix metalloproteinase (MMP), of which a variety are known. In general, known inhibitors of MMPs are chemically modified tetracyclines (CMTs), a number of which are listed below. The structure of tetracycline is shown below in Structure 1:

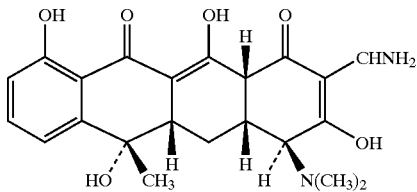

Structure 1

As will be appreciated by those in the art, and as described herein, any number of functional groups (either endogeneous to the structure or added exogeneously) can be used to attach these derivatives, and all those outlined herein, to the chelates. The CMTs include, but are not limited to, 4-dimethylamino-TC (also known as CMT-1); tetracycinonitrile (CMT-2); 6-demethyl, 6-deoxy, 4-dedimethylamino-TC (CMT-3); 7-chloro, 4-dedimethylamino-TC (CMT-4); 4-hydroxy, 4-dedimethylamino-TC (CMT-6); 12α-deoxy, 5-hydroxy-4-dedimethylamino-TC (CMT-7); 6α-deoxy, 5-hydroxy-4-dedimethylamino-TC (CMT-8); 12α, 4α-anhydro, 4-dedimethylamino-TC (CMT-9); 7-dimethylamino, 4-dedimethylamino-TC (CMT-10). In addition to the CMTs, other known inhibitors of MMPs include the tissue inhibitors of MPs-1 and MPs-2 (TIMP-1 and TIMP-2, respectively) and minocycline (Min) and doxycycline (Dox), shown in Structures 2 and 3, respectively.

Structure 2

Structure 3

In addition, there are a number of other MMP inhibitors and substrates that can be used. The substrates are particularly useful as cancer cleavage sites with the use of coordination site barriers. These MMP inhibitors and substrates include, but are not limited to, 1, 10-phenanthroline; CT 1847; AG3319, AG3340 (also called Prinomastat), AG3287, AG3293, AG3294, AG3296; 2-mercaptoacetyl-L-phenylalanyl-L-leucine; HSCH$_2$—CH[CH$_2$CH(CH$_3$)$_2$]CO-Phe-Ala-NH$_2$; OPB-3206; Furin Inhibit 3,4-dihydro-1-oxo-1,2,3,-benzotriazine-3-(3-tetrahydrofuranyl)carbonate (LW-1); 1,2-dihydro-3,6-dioxo-2-phenyl-pyridazine-1-methylcarbonate (LW-2); 3,4-dihydro-1-oxo-1,2,3,-benzotriazine-3-(2-methoxy)ethylcarbonate (LW-3); 1,2-dihydro-2-ethoxycarbonyl-(1-oxo-isochinolin-5-yl) ethylcarbonate (LW-4); 1(2H)-phtalazinone-2-(4-methoxyphenyl)carbonate (LW-5); N-[2(R)-2-(hydroxamido carbonylmethyl)4-methylpentanoyl]-L-tryptophane methylamide also called GM6001, Galardin and ilomastat; BAY 12-9566; Neovastat (AE-941); BB-1101; GI129471; Ph(CH$_2$NH-D-R$_{rev}$—CO—CH$_2$CH$_2$-D)$_2$ also called FC-336; Mca-Pro-Leu-Gly-Leu-Dpa-Ala-Arg-NH$_2$ (cleavage occurs between Gly and Leu); DNP-Pro-Leu-Gly-Ile-Ala-Gly-Arg-COOH (cleavage occurs between Gly and Leu); arboxymethyl transferrin (Cm-Tf); (7-methoxycoumarin-4-yl)acetyl-PLGP-[3-(2,4-dinitrophenyl)-L-2,3-diaminopropionyl]-AR-$NH_2$; (7-methoxycoumarin-4-yl)acetyl-PLAQAV-[3-(2,4-dinitrophenyl)-L-2,3-diaminopropionyl]-RSSSR-$NH_2$; Ac-PLG-[2-mercapto-4-methylpentanoyl]-LG-OEt; Peptide I: GPLGLRSW; and Peptide II: GPLPLRSW. See generally, Greenwald, R. A. et al. In vitro sensitivity of the three mammalian collagenases to tetracycline inhibition: relationship to bone and cartilage degradation. *Bone* 22, 33–38 (1998); Kolb, S. A. et al. Matrix metalloproteinases and tissue inhibitors of metalloproteinases in viral meningitis: upregulation of MMP-9 and TIMP-1 in cerebrospinal fluid. *J. Neuroimmunol.* 84, 143–150 (1998); Charoenrat, P. et al. Overexpression of epidermal growth factor receptor in human head and neck squamous carcinoma cell lines correlates with matrix metalloproteinase-9 expression and in vitro invasion. *Int. J. Cancer* 86, 307–317 (2000); Uzui, H., Lee, J. D., Shimizu, H., Tsutani, H. & Ueda, T. The role of protein-tyrosine phosphorylation and gelatinase production in the migration and proliferation of smooth muscle cells. *Atherosclerosis* 149, 51–59 (2000); Montesano, R., Soriano, J. V., Hosseini, G., Pepper, M. S. & Schramek, H. Constitutively active mitogen-activated protein kinase kinase MEK1 disrupts morphogenesis and induces an invasive phenotype in Madin-Darby canine kidney epithelial cells. *Cell Growth Differ.* 10, 317–332 (1999); Yip, D., Ahmad, A., Karapetis, C. S., Hawkins, C. A. & Harper, P. G. Matrix metalloproteinase inhibitors: applications in oncology. *Invest New Drugs* 17, 387–399 (1999); Price, A. et al. Marked inhibition of tumor growth in a malignant glioma tumor model by a novel synthetic matrix metalloproteinase inhibitor AG3340. *Clin. Cancer Res.* 5, 845–854 (1999); Santos, O., McDermott, C. D., Daniels, R. G. & Appelt, K. Rodent pharmacokinetic and anti-tumor efficacy studies with a series of synthetic inhibitors of matrix metalloproteinases. *Clin. Exp. Metastasis* 15, 499–508 (1997); Barletta, J. P. et al. Inhibition of pseudomonal ulceration in rabbit corneas by a synthetic matrix metalloproteinase inhibitor. *Invest Ophthalmol. Vis. Sci.* 37, 20–28 (1996); Maquoi, E. et al. Inhibition of matrix metalloproteinase 2 maturation and HT1080 invasiveness by a synthetic furin inhibitor. *FEBS Lett.* 424, 262–266 (1998); Makela, M. et al. Matrix metalloproteinase 2 (gelatinase A) is related to migration of keratinocytes. *Exp. Cell Res.* 251, 67–78 (1999); Hao, J. L. et al. Effect of galardin on collagen degradation by Pseudomonas aeruginosa. *Exp. Eye Res.* 69, 595–601 (1999); Hao, J. L. et al. Galardin inhibits collagen degradation by rabbit keratocytes by inhibiting the activation of pro-matrix metalloproteinases. *Exp. Eye Res.* 68, 565–572 (1999); Wallace, G. R. et al. The matrix metalloproteinase inhibitor BB-1101 prevents experimental autoimmune uveoretinitis (EAU). *Clin. Exp. Immunol.* 118, 364–370 (1999); Maquoi, E. et al. Membrane type 1 matrix metalloproteinase-associated degradation of tissue inhibitor of metalloproteinase 2 in human tumor cell lines. *J. Biol. Chem.* 275, 11368–11378 (2000); Ikeda, T. et al. Anti-invasive activity of synthetic serine protease inhibitors and its combined effect with a matrix metalloproteinase inhibitor. *Anticancer Res.* 18, 4259–4265 (1998); Schultz, G. S. et al. Treatment of alkali-injured rabbit corneas with a synthetic inhibitor of matrix metalloproteinases. *Invest Ophthalmol. Vis. Sci.* 33, 3325–3331 (1992); Buchardt, J. et al. Phosphinic Peptide Matrix Metalloproteinase-9 Inhibitors by Solid-Phase Synthesis Using a Building Block Approach. *Chem. Eur. J.* 5, 2877–2884 (2000); Dahlberg, L. et al. Selective enhancement of collagenase-mediated cleavage of resident type II collagen in cultured osteoarthritic cartilage and arrest with a synthetic inhibitor that spares collagenase 1 (matrix metalloproteinase 1). *Arthritis Rheum.* 43, 673–682 (2000); Lombard, M. A. et al. Synthetic matrix metalloproteinase inhibitors and tissue inhibitor of metalloproteinase (TIMP)-2, but not TIMP-1, inhibit shedding of tumor necrosis factor-alpha receptors in a human colon adenocarcinoma (Colo 205) cell line. *Cancer Res.* 58, 4001–4007 (1998); Lein, M. et al. Synthetic inhibitor of matrix metalloproteinases (batimastat) reduces prostate cancer growth in an orthotopic rat model. *Prostate* 43, 77–82 (2000); Brown, P. D. Matrix metalloproteinase inhibitors in the treatment of cancer. *Med. Oncol.* 14, 1–10 (1997); Garbett, E. A., Reed, M. W. & Brown, N. J. Proteolysis in colorectal cancer. *Mol. Pathol* 52, 140–145 (1999); Itoh, M. et al. Purification and refolding of recombinant human proMMP-7 (pro-matrilysin) expressed in Escherichia coli and its characterization. *J. Biochem.* (Tokyo) 119, 667–673 (1996); Wang, Y., Johnson, A. R., Ye, Q. Z. & Dyer, R. D. Catalytic activities and substrate specificity of the human membrane type 4 matrix metalloproteinase catalytic domain. *J. Biol. Chem.* 274, 33043–33049 (1999); Ohkubo, S. et al. Identification of substrate sequences for membrane type-1 matrix metalloproteinase using bacteriophage peptide display library. *Biochem. Biophys. Res. Commun.* 266, 308–313 (1999), all of which are expressly incorporated by reference; the structures of some of these are shown in FIG. 7.

In a preferred embodiment, the TAAGM is a substrate or inhibitor for matrilysin (also sometimes referred to in the literature as pump-1 and MMP-7). It has been implicated in gastric, colon, breast and prostate cancers, and is clearly implicated in metastasis and potentially growth and invasion as well. It is a zinc metalloenzyme, with a thermolysin-type Zn binding region), and is activated by cystein switch. It is exclusively associated with tumor cells, unlike other MMPS, and its mRNA expression is induced by IL-1β. It is secreted from epithelial cells of glandular tissue. Its substrates include, but are not limited to, proteglycans, laminin, fibronectin, gelatins, collagen IV, elastin, entactin and tenascin. Its inhibitors include a variety of metal chelators and tissue inhibitors (TIMPs). See MacDougall et al., Cancer and Metastasis Rev. 14:351 (1995); Stetler-Stevenson et al., FASEB 7:1434 (1993); Mirelle Gaire et al., J. Biol. Chem. 269:2032 (1994), all of which are expressly incorporated by reference.

In a preferred embodiment, the TAAGM is a substrate or inhibitor for the extracellular statum corneum chymotryptic enzyme (SCCE), which has been implicated in ovarian cancer. This enzyme is involved in tumor invasion and metastasis by allowing implantation and invasion of neighboring cells. It is a serine protease with a standard catalytic triad (ser-his-asp) in its active site, and it may activate MMPs. Its substrates include gelatin and collagen, and is inhibited by the D43 mAb. See Tantimoto et al., supra; Hansson et al., J. Biol. Com. 269:19420 (1994), both of which are incorporated by reference.

In a preferred embodiment, the TAAGM is a substrate or inhibitor for seprase. Seprase has been implicated in breast cancer and is involved in an early event in the progression from a non-invasive premalignant phenotype to the invasive malignant phenotype. It is a 170 kDa dimer, and is a serine integral membrane protease (with a putative standard catalytic triad) with gelanitinase activity. The monomer 97 kDa form is inactive. The catalytic domain is exposed to the extracellular environment. Seprase is overexpressed in neoplasic invasive ductal carcinoma (IDC) cells and exhibits low levels of expression in benign proliferative tissue or normal breast cells. It also may activate MMPs. It degrades gelatin and collagen. See Kelly et al, Mod. Path. 11 (9):855 (1998), incorporated by reference.

In a preferred embodiment, the TAAGM is a substrate or inhibitor for Type IV collegenase (also sometimes referred to as MMP-2 and gelantinase A). This enzyme has been implicated in breast, colon and gastic cancers, and is involved in the penetration of membrane material and the invasion of stroma. It is a 72 kDa neutral Zn metalloendoproteinase that degrades basement membrane type IV collagen and gelatin in a pepsin-resistant domain. It is activated by a cysteine switch and is a membrane type I MMP. It is secreted extracellularly by epithelial cells, fibroblasts, endothelial cells and macrophages as an inactivaled form. Its substrates include, but are not limited to, type IV collagen, gelatins, fibroblasts, type V collagens, type VII collagen, proMMP-9 and elastins. It's inhibitors include TIMP-2. See Poulsom et al., Am. J. Path. 141:389 (1992); Stearns et al., Cancer Res. 53:878 (1993); Nakahara et al., PNAS USA 94:7959 (1997); and Johnson et al., Curr. Opin. Chem. Biol. 2:466 (1999), all of which are expressly incorporated by reference.

In a preferred embodiment, the TAAGM is a substrate or inhibitor of HER-2/neu protein (sometimes referred to as erb-B-2). HER-2/neu is a 185 kDa transmembrane phosphoglycoprotein with tyrosine kinase activity that has been implicated in breast, ovarian and non-small cell (NSC) lung carcinoma. High serum levels have been shown to correlate with poor prognosis and increased resistance to endocrine therapy, and it has been identified in 25–30% of all breast cancers. Its ligands are NDF/heregulins and gp 30 (which is related to TGFα. See Codony-Serat et al., Cancer Res. 59:1196 (1999); Earp et al., Breast Canc. Res. Treat. 35:115 (1995); Depowski et al., Am. J. Clin. Pathol. 112:459 (1999), all of which are expressly incorporated by reference.

In a preferred embodiment, the TAAGM binds and/or inhibits ras, which has been implicated in NSC lung cancer. Ras is an essential signal transduction protein though to follow overexpression of HER2/neu protein, and is also related to p53 overexpression. Deregulated expression of ras results in uncontrolled cell growth and cancer, with overexpression being correlated with drug resistance. It functions as a surface antigen that is recognized by antibodies and T-cells. See Shackney et al., J. Thorac. Cadio. Surg 118:259 (1999), incorporated by reference.

In a preferred embodiment, the TAAGM binds to RCAS1. RCAS1 has been implicated in uterine, ovarian, esophageal and small cell lung carcinomas, gastic colon, lung and pancreatic cancers. It is a type II membrane protein and acts as aligand for a receptor on normal peripheral lymphocytes (e.g. T and NK cells) followed by inhibition of the receptor cell and cell death. It neutralizes immunoprotection by lymphocytes. It is expressed on cancer cell surfaces and in the extracellular medium, but is not detected in normal cells. See Nakashima et al., Nature Med. 5:938 (1999) and Villunger et al., Nature Medicine 5:874 (1999), incorporated by reference.

In a preferred embodiment, the TAAGM binds to reg protein (including regIα and regIβ and pap). Reg has been implicated in pancreatic cancer, colorectal and liver carcinomas, and is present in acinar cell carcinoma, pancreatoblastoma, solid and cystic tumors and ductal cell carcinoma. See Rechreche et la., Int. J. Cancer 81:688 (1999) and Kimura et al., Cancer 70:1857 (1992), incorporated by reference.

In a preferred embodiment, the TAAGM binds to thrombospondin-1, which has been implicated in pancreatic adenocarcinoma. It activates TGF-β, which is a key fibrogenic factor resulting in desmoplasia. See Cramer et al, Gastrent. 166 (4 pt 2):pA1116 (G4840) (1999); incorporated by reference.

In a preferred embodiment, the TAAGM is a substrate or inhibitor for a caspase enzyme, including caspase-1 (also sometimes referred to as IL-1β), -3, -8, -9, etc. Caspases are also cysteine proteases which are putatively involved in the apoptosis cascade. Many of the caspases are generally made as proenzymes of 30–50 kDa. They cleave after asp residues with recognition of 4 amino acids on the N-side of the cleavage site.

In a preferred embodiment, the TAAGM binds to alpha 1-acid glycoprotein (AAG). AAG has been suggested as a prognostic aid for glioma and metastatic breast and other carcinomas. AAG is highly soluble and is a single 183 amino acid polypeptide chain. It is characterized by a high carbohydrate (45%) and sialic acid (12%) content, and a low isoelectric point (pH 2.7). It has been implicated in binding of many drugs, including propranolol, imipramine and chloropromazine, all of which can be used as a guarding moiety.

In a preferred embodiment, the TAAGM is involved in angiogenesis. There are a wide variety of moieties known to be involved in angiogenesis, including, but not limited to, vascular endothelial growth factors (VEGF; including VEGF-A, VEGF-B, VEGF-C and VEGF-D), FGF-1 (aFGF), FGF-2 (bFGF), FGF-3, FGF-4, hepatocyte growth factor (HGF, scatter factor), thymidine phosphorylase, angiogenin, IL-8, TNF-α, leptin, transforming growth factors (TGF-α, TGF-β), platelet-derived growth factor, proliferin, and granulocyte colony stimulating factor (G-CSF). Known angiogenesis inhibitors include, but are not limited to, platelet factor 4, thrombospondin-1, interferons (IFN-α, IFN-β, IFN-γ), IL-1, IL-2, vascular endothelial growth inhibitor (VEGI), 2-methoxyestradiol, tissue inhibitors of MMPs (TIMPs), proliferin related protein, angiostatin, endostatin, amion terminal fragment of u-PA (ATF), thalidomide, TNP-470/AGM-1470, carboxyamidotriazole, maspin, AG3340, marimastat, BAY9566, CSG-27023A, gly-arg-gly-asp-ser (GRGDS), tyr-ile-gly-ser-arg (YIGSR) and ser-ile-lys-val-ala-val (SIKVAV). See van Hinsbergh et al, Annals of Oncology 10 Supp. 4:60 (1999) and references therein; Li et al., Human Gene Therapy 10(18):3045 (1999); Duenas et al., Investigative Ophthalmology, 1999; Bauer et al., J. Pharmacology & Experimental Therapeutics 292(1):31 (2000); Zhang et al., Nature Medicine 6(2):196 (2000); Sipose et al., Annal of the New York Academy of Sciences 732:263 (1994 and references therein); Niresia et al, Am. J. Pathology 138(4):829 (1991); Yamamura et al., Seminars in Cancer Biology 4(4):259 (1993).

As will be appreciated by those skilled in the art, the potential list of suitable cancer enzyme targets is quite large.

Once the target cancer enzyme is identified or chosen, enzyme substrate TAAGMs can be designed using well known parameters of enzyme substrate specificities as is generally known in the art.

For example, when the enzyme cancer target substance is a protease, the guarding moiety may be a peptide or polypeptide which is capable of being cleaved by the target cancer protease. By "peptide" or "polypeptide" herein is meant a compound of about 2 to about 15 amino acid residues covalently linked by peptide bonds. Preferred embodiments utilize polypeptides from about 2 to about 8 amino acids, with about 2 to about 4 being the most preferred. Preferably, the amino acids are naturally occurring amino acids, although amino acid analogs and peptidomimitic structures are also useful, particularly in the design of inhibitors. Under certain circumstances, the peptide may be only a single amino acid residue.

Similarly, when the enzyme cancer target substance is a carbohydrase, the TAAGM will be a carbohydrate group which is capable of being cleaved by the target carbohydrase.

In another embodiment, the TAAGM may be an enzyme inhibitor, such that in the presence of the enzyme, the inhibitor TAAGM disassociates from the metal ion complex to interact or bind to the enzyme, thus freeing an inner coordination sphere site of the metal ion for interaction with water. As above, the enzyme inhibitors are chosen on the basis of the enzyme cancer target substance and the corresponding known characteristics of the enzyme.

In a preferred embodiment, the TAAGM is a phosphorus moiety, as defined above, such as $-(OPO(OR_2))_n$, wherein n is an integer from 1 to about 10, with from 1 to 5 being preferred and 1 to 3 being particularly preferred. Each R is independently hydrogen or a substitution group as defined herein, with hydrogen being preferred. This embodiment is particularly useful when the target molecule is alkaline phosphatase or a phosphodiesterase, or other enzymes known to cleave phosphorus containing moieties such as these.

In one embodiment, the TAAGM is a nucleic acid. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp169–176). Several nucleic acid analogs are described in Rawls, C & E News June 2, 1997 page 35. All of these references are hereby expressly incorporated by reference. These modifications of the ribose-phosphate backbone may be done to facilitate the addition of electron transfer moieties, or to increase the stability and half-life of such molecules in physiological environments.

As will be appreciated by those in the art, all of these nucleic acid analogs may find use in the present invention. In addition, mixtures of naturally occurring nucleic acids and analogs can be made, or mixtures of different nucleic acid analogs, and mixtures of naturally occurring nucleic acids and analogs may be made.

Alternatively, as is generally described in U.S. Pat. Nos. 5,270,163, 5,475,096, 5,567,588, 5,595,877, 5,637,459, 5,683,867, 5,705,337, and related patents, hereby incorporated by reference, nucleic acid "aptamers" can be developed for binding to virtually any target analyte; thus for example, aptamers may be developed to a wide variety of cancer moieties.

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc. As used herein, the term "nucleoside" includes nucleotides and nucleoside and nucleotide analogs, and modified nucleosides such as amino modified nucleosides. In addition, "nucleoside" includes non-naturally occuring analog structures. Thus for example the individual units of a peptide nucleic acid, each containing a base, are referred to herein as a nucleoside. The target molecule can be a substantially complementary nucleic acid or a nucleic acid binding moiety, such as a protein.

In a preferred embodiment, the TAAGM is a ligand for a cell-surface receptor involved in cancer or is a ligand which has affinity for a extracellular component that is involved in cancer. In this embodiment, the ligand has sufficient affinity for the metal ion to prevent the rapid exchange of water molecules in the absence of the cancer target substance. Alternatively, there may be R groups "locking" the ligand into place, as described herein, resulting in either the contribution of a coordination atom or that the ligand serves as a coordination site barrier. In this embodiment the ligand TAAGM has a higher affinity for the cancer target substance than for the metal ion. Accordingly, in the presence of the cancer target substance, the ligand TAAGM will interact with the cancer target substance, thus freeing up at least one coordination site in the metal ion complex and allowing the rapid exchange of water and an increase in relaxivity. Additionally, in this embodiment, this may result in the accumulation of the MRI agent at the location of the target, for example at the cell surface. This may be similar to the situation where the TAAGM is an enzyme inhibitor, as well.

In this embodiment, the TAAGM may be all or a portion (e.g. a binding portion) of a ligand for a cell surface receptor. Suitable ligands include, but are not limited to, all or a functional portion of the ligands that bind to a cell surface receptor that is differentially expressed in a cancerous cell; these may vary from cancer to cancer, but can include ligands selected from the group consisting of ligand that bind to: insulin receptor (insulin), insulin-like growth factor receptor (including both IGF-1 and IGF-2), growth hormone receptor, estrogen receptor; glucose transporters (particularly GLUT 4 receptor), transferrin receptor (transferrin), epidermal growth factor receptor (EGF), low density lipoprotein receptor, high density lipoprotein receptor, leptin receptor, interleukin receptors including IL-1, IL-2, IL-3, IL-4, IL-5, IL-6, IL-7, IL-8, IL-9, IL-11, IL-12, IL-13, IL-15, and IL-17 receptors, human growth hormone receptor, VEGF receptor (VEGF), PDGF receptor (PDGF), transforming growth factor receptor (including TGF-α and TGF-β), EPO receptor (EPO), TPO receptor (TPO), ciliary neurotrophic factor receptor, prolactin receptor, and T-cell receptors. In particular, hormone ligands are preferred. Hormones include both steroid hormones and proteinaceous hormones, including, but not limited to, epinephrine, thyroxine, oxytocin, insulin, thyroid-stimulating hormone, calcitonin, chorionic gonadotropin, cortictropin, follicle-stimulating hormone, glucagon, leuteinizing hormone, lipotropin, melanocyte-stimutating hormone, norepinephrine, parathryroid hormone, thyroid-stimulating hormone (TSH), vasopressin, enkephalins, seratonin, estradiol, progesterone, testosterone, cortisone, glucocorticoids and the hormones above. Receptor ligands include ligands that bind to receptors such as cell surface receptors, which include hormones, lipids, proteins, glycoproteins, signal transducers, growth factors, cytokines, and others.

In a preferred embodiment, the TAAGM is a photocleavable moiety. That is, upon exposure to a certain wavelength of light, the guarding moiety is cleaved, allowing an increase in the exchange rate of water in at least one coordination site of the complex. This embodiment has particular use in developmental biology fields (cell lineage, neuronal development, etc.), where the ability to follow the fates of particular cells is desirable. Suitable photocleavable moieties are similar to "caged" reagents which are cleaved upon exposure to light. A particularly preferred class of photocleavable moieties are the O-nitrobenzylic compounds, which can be synthetically incorporated into a blocking moiety via an ether, thioether, ester (including phosphate esters), amine or similar linkage to a heteroatom (particularly oxygen, nitrogen or sulfur). Also of use are benzoin-based photocleavable moieties. A wide variety of suitable photocleavable moieties is outlined in the Molecular Probes Catalog, supra.

In a preferred embodiment, the compounds have a structure depicted below in Structure 4, which depicts a nitrobenzyl photocleavable group, although as will be appreciated by those in the art, a wide variety of other moieties may be used:

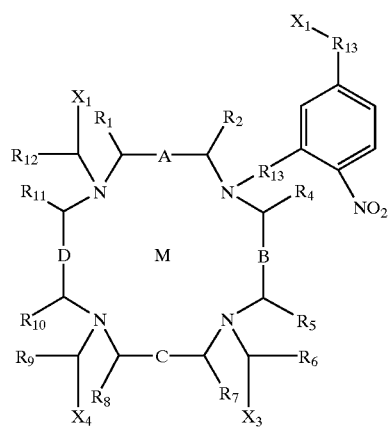

Structure 4

Structure 4 depicts a DOTA-type chelator, although as will be appreciated by those in the art, other chelators may be used as well. $R_{13}$ is a linker as defined below. Similarly, the $X_2$ group may be as defined above, although additional structures may be used, for example a coordination site barrier as outlined herein. Similarly, there may be substitutent groups on the aromatic ring, as is known in the art.

The TAAGM itself may block or occupy at least one coordination site of the metal ion. That is, one or more atoms of the TAAGM (i.e. the enzyme substrate, ligand, moiety which interacts with a cell-surface receptor, etc) itself serves as a coordination atom, or otherwise blocks access to the metal ion by steric hinderance. For example, it appears that one or more of the atoms of the carbohydrate moiety TAAGM outlined in the Examples may be direct coordination atoms for the Gd(III) metal ion. Similarly, peptide based TAAGMs for protease targets may contribute coordination atoms.

In an alternative embodiment, the TAAGM further comprises a "coordination site barrier" which is covalently tethered to the complex in such a manner as to allow disassociation upon interaction with a cancer target substance. For example, it may be tethered by one or more enzyme substrate TAAGMs. In this embodiment, the coordination site barrier blocks or occupies at least one of the coordination sites of the metal ion in the absence of the target enzyme substance. Coordination site barriers are used when coordination atoms are not provided by the functional portion of the TAAGM, i.e. the component of the TAAGM which interacts with the cancer target substance. The TAAGM or moieties such as an enzyme substrate serves as the tether, covalently linking the coordination site barrier to the metal ion complex. In the presence of the enzyme target, the enzyme cleaves one or more of the enzyme substrates, either within the substrate or at the point of attachment to the metal ion complex, thus freeing the coordination site barrier. The coordination site or sites are no longer blocked and the bulk water is free to rapidly exchange at the coordination site of the metal ion, thus enhancing the image. As will be appreciated by those in the art, a similar result can be accomplished with other types of TAAGMs.

In one embodiment, the coordination site barrier is attached to the metal ion complex at one end, as is depicted in FIG. 4. When the enzyme target cleaves the substrate TAAGM, the coordination site barrier is released. In another embodiment, the coordination site barrier is attached to the metal ion complex with more than one substrate TAAGM, as is depicted in FIG. 5 for two attachments. The enzyme target may cleave only one side, thus removing the coordination site barrier and allowing the exchange of water at the coordination site, but leaving the coordination site barrier attached to the metal ion complex. Alternatively, the enzyme may cleave the coordination site barrier completely from the metal ion complex.

In a preferred embodiment, the coordination site barrier occupies at least one of the coordination sites of the metal ion. That is, the coordination site barrier contains at least one atom which serves as at least one coordination atom for the metal ion. In this embodiment, the coordination site barrier may be a heteroalkyl group, such as an alkyl amine group, as defined above, including alkyl pyridine, alkyl pyrroline, alkyl pyrrolidine, and alkyl pyrole, or a carboxylic or carbonyl group. The portion of the coordination site barrier which does not contribute the coordination atom may also be consider a linker group. Preferred coordination site barriers are depicted in FIG. 4.

In an alternative embodiment, the coordination site barrier does not directly occupy a coordination site, but instead blocks the site sterically. In this embodiment, the coordination site barrier may be an alkyl or substituted group, as defined above, or other groups such as peptides, proteins, nucleic acids, etc.

In this embodiment, the coordination site barrier is preferably linked via two enzyme substrates to opposite sides of the metal ion complex, effectively "stretching" the coordination site barrier over the coordination site or sites of the metal ion complex, as is depicted in FIG. 5.

In some embodiments, the coordination site barrier may be "stretched" via an enzyme substrate on one side, covalently attached to the metal ion complex, and a linker moiety, as defined below, on the other. In an alternative embodiment, the coordination site barrier is linked via a single enzyme substrate on one side; that is, the affinity of the coordination site barrier for the metal ion is higher than that of water, and thus the TAAGM, comprising the coordination site barrier and the enzyme substrate, will block or occupy the available coordination sites in the absence of the target enzyme. In some embodiments, the metal ion complexes of the invention have a single associated or bound TAAGM. In such embodiments, the single TAAGM impedes the exchange of water molecules in at least one coordination site. Alternatively, as is outlined below, a single TAAGM may hinder the exchange of water molecules in more than one coordination site, or coordination sites on different chelators.

In alternative embodiments, two or more TAAGMs are associated with a single metal ion complex, to impede the exchange of water in at least one or more coordination sites.

It should be appreciated that the TAAGMs of the present invention may further comprise a linker group as well as a functional TAAGM. That is, TAAGMs may comprise functional TAAGMs in combination with a linker group and/or a coordination site barrier.

Linker groups (sometimes depicted herein as $R_{13}$) will be used to optimize the steric considerations of the metal ion complex. That is, in order to optimize the interaction of the TAAGM with the metal ion, linkers may be introduced to allow the functional TAAGM to block or occupy the coordination site. In general, the linker group is chosen to allow a degree of structural flexibility. For example, when a TAAGM interacts with a physiological agent which does not result in the TAAGM being cleaved from the complex, the linker must allow some movement of the TAAGM away from the complex, such that the exchange of water at at least one coordination site is increased.

Generally, suitable linker groups include all R groups listed above (with the exception of hydrogen). Preferred groups include, but are not limited to, alkyl and aryl groups, including substituted alkyl and aryl groups and heteroalkyl (particularly oxo groups) and heteroaryl groups, including alkyl amine groups, as defined above. Preferred linker groups include p-aminobenzyl, substituted p-aminobenzyl, diphenyl and substituted diphenyl, alkyl furan such as benzylfuran, carboxy, and straight chain alkyl groups of 1 to 10 carbons in length. Particularly preferred linkers include p-aminobenzyl, methyl, ethyl, propyl, butyl, pentyl, hexyl, acetic acid, propionic acid, aminobutyl, p-alkyl phenols, 4-alkylimidazole, carbonyls, OH, COOH, glycols, etc.

The selection of the linker group is generally done using well known molecular modeling techniques, to optimize the obstruction of the coordination site or sites of the metal ion. In addition, as outlined in the Examples, the length of this linker may be very important in order to achieve optimal results. The length of the linker, i.e the spacer between the chelator and the coordination atom(s) of the TAAGM, can contribute to the steric conformation and association of the coordination atoms with the metal ion, thus allowing excellent blocking of the metal ion by the TAAGM.

The TAAGM is attached to the metal ion complex in a variety of ways. In a preferred embodiment, as noted above, the TAAGM is attached to the metal ion complex via a linker group. Alternatively, the TMGM is attached directly to the metal ion complex; for example, as outlined below, the TAAGM may be a substituent group on the chelator.

In a preferred embodiment at least one of the R groups attached to the "arms" of the chelator, for example $R_3$, $R_6$, $R_9$ or $R_{12}$ of the DOTA structures, or $R_{14}$, $R_{15}$, $R_{18}$, $R_{21}$ or $R_{22}$ of the DTPA structures, comprises an alkyl (including substituted and heteroalkyl groups), or aryl (including substituted and heteroaryl groups), i.e. is a group sterically bulkier than hydrogen. This is particular useful to drive the equilibrium towards "locking" the coordination atom of the arm into place to prevent water exchange, as is known for standard MRI contrast agents. Preferred groups include the C1 through C10 alkyl groups with methyl being particularly preferred, including heteroatoms.

This is particularly preferred when the TAAGM is attached via one of the "arms", for example when a TAAGM is at position $X_1$ to $X_4$.

However the inclusion of too many groups may drive the equilibrium in the other direction effectively locking the coordination atom out of position. Therefore in a preferred embodiment only 1 or 2 of these positions is a non-hydrogen group, unless other methods are used to drive the equilibrium towards binding.

The TAAGMs are chosen and designed using a variety of parameters. In the embodiment which uses a coordination site barrier, i.e. when the functional group of the TAAGM does not provide a coordination atom, and the coordination site barrier is fastened or secured on two sides, the affinity of the coordination site barrier of the TAAGM for the metal ion complex need not be great, since it is tethered in place. That is, in this embodiment, the complex is "off" in the absence of the cancer target substance. However, in the embodiment where the TAAGM is linked to the complex in such a manner as to allow some rotation or flexibility of the TAAGM, for example, it is linked on one side only, such as the embodiment of the examples, the TAAGM should be designed such that it occupies the coordination site a majority of the time. To this end, adding steric groups to the other "arms" of the chelator may serve to "lock" the coordination atoms of the arms, to reduce the rotational freedom of the group and thus effectively drive the equilibrium to the "off" position, and thus result in a larger percentage increase in the signal in the presence of the target. See U.S. Pat. No. 5,980,862, hereby expressly incorporated by reference.

When the TAAGM is not covalently tethered on two sides, as is depicted in FIG. 5, it should be understood that TAAGMs and coordination site barriers are chosen to maximize three basic interactions that allow the TAAGM to be sufficiently associated with the complex to hinder the rapid exchange of water in at least one coordination site of the complex. First, there may be electrostatic interactions between the TMGM and the metal ion, to allow the TMGM to associate with the complex. Secondly, there may be Van der Waals and dipole-dipole interactions. Thirdly, there may be ligand interactions, that is, one or more functionalities of the TAAGM may serve as coordination atoms for the metal. In addition, linker groups may be chosen to force or favor certain conformations, to drive the equilibrium towards an associated TAAGM. Similarly, removing degrees of fredom in the molecule may force a particular conformation to prevail. Thus, for example, the addition of alkyl groups, and particularly methyl groups, at "arm" positions when the TAAGM is attached at the arm position can lead the TAAGM to favor the blocking position. Similar restrictions can be made in the other embodiments, as will be appreciated by those in the art.

Furthermore, effective "tethering" of the TAAGM down over the metal ion may also be done by engineering in other non-covalent interactions that will serve to increase the affinity of the TAAGM to the chelator complex, as is depicted below.

Potential TAAGMs may be easily tested to see if they are functional; that is, if they sufficiently occupy or block the appropriate coordination site or sites of the complex to prevent rapid exchange of water. Thus, for example, complexes are made with potential TAAGMs and then compared with the chelator without the TAAGM in imaging experiments. Once it is shown that the TAAGM is a sufficient "blocker", the cancer target substance is added and the experiments repeated, to show that interaction with the cancer target substance increases the exchange of water and thus enhances the image.

In addition to the TAAGMs outlined herein, the compositions of the invention may optionally have at least one targeting moiety. That is, a targeting moiety may be attached at any of the R positions (or to a linker, including a polymer, or to a TAAGM, etc., as is more fully described below). In some embodiments, the targeting moiety replaces a coordination atom, although this is not generally preferred in clinical applications, as this may increase toxicity. By "targeting moiety" herein is meant a functional group which serves to target or direct the complex to a particular location, cell type, diseased tissue, or association. In general, the targeting moiety is directed against a target molecule. As will be appreciated by those in the art, the MRI contrast agents of the invention are generally injected intraveneously; thus preferred targeting moieties are those that allow concentration of the agents in a particular localization. In a preferred embodiment, the agent is partitioned to the location in a non-1:1 ration. Thus, for example, antibodies, cell surface receptor ligands and hormones, lipids, sugars and dextrans, alcohols, bile acids, fatty acids, amino acids, peptides and nucleic acids may all be attached to localize or target the contrast agent to a particular site.

In a preferred embodiment, the targeting moiety allows targeting of the MRI agents of the invention to a particular tissue, the surface of a cell or a subcellular location. That is, in a preferred embodiment the MRI agents of the invention need not be taken up into the cytoplasm of a cell to be activated.

In a preferred embodiment, the targeting moiety is a peptide. For example, chemotactic peptides have been used to image tissue injury and inflammation, particularly by bacterial infection; see WO 97/14443, hereby expressly incorporated by reference in its entirety.

In a preferred embodiment, the targeting moiety is an antibody. The term "antibody" includes antibody fragments, as are known in the art, including Fab Fab$_2$, single chain antibodies (Fv for example), chimeric antibodies, etc., either produced by the modification of whole antibodies or those synthesized de novo using recombinant DNA technologies.

In a preferred embodiment, the antibody targeting moieties of the invention are humanized antibodies or human antibodies. Humanized forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature 321:522–525 (1986); Riechmann et al., Nature 332:323–329 (1988); and Presta, Curr. Op. Struct. Biol. 2:593–596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., Nature 321:522–525 (1986); Riechmann et al., Nature 332:323–327 (1988); Verhoeyen et al., Science 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol. 227:381 (1991); Marks et al., J. Mol. Biol. 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol. 147(1):86–95 (1991)]. Similarly, human antibodie can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10:779–783 (1992); Lonberg et al., Nature 368:856–859 (1994); Morrison, Nature 368:812–13 (1994); Fishwild et al., Nature Biotechnology 14:845–51 (1996); Neuberger, Nature Biotechnology, 14:826 (1996); Lonberg and Huszar, Intern. Rev. Immunol. 13:65–93 (1995).

Bispecific antibodies are monoclonal, preferably human or humanized, antibodies that have binding specificities for at least two different antigens. In the present case, one of the binding specificities is for a first target molecule and the other one is for a second target molecule.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, Nature 305:537–539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., EMBO J. 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology 121:210 (1986).

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

In a preferred embodiment, the antibody is directed against a cell-surface marker on a cancer cell; that is, the target molecule is a cell surface molecule. As is known in the art, there are a wide variety of antibodies known to be differentially expressed on tumor cells.

In addition, antibodies against physiologically relevant carbohydrates may be used, including, but not limited to, antibodies against markers for breast cancer (CA15-3, CA549, CA27.29), mucin-like carcinoma associated antigen (MCA), ovarian cancer (CA125), pancreatic cancer (DE-PAN-2), and colorectal and pancreatic cancer (CA19, CA50, CA242).

In one embodiment, antibodies against virus or bacteria can be used as targeting moieties. As will be appreciated by those in the art, antibodies to any number of viruses (including orthomyxoviruses, (e.g. influenza virus), paramyxoviruses (e.g respiratory syncytial virus, mumps virus, measles virus), adenoviruses, rhinoviruses, coronaviruses, reoviruses, togaviruses (e.g. rubella virus), parvoviruses, poxviruses (e.g. variola virus, vaccinia virus), enteroviruses (e.g. poliovirus, coxsackievirus), hepatitis viruses (including A, B and C), herpesviruses (e.g. Herpes simplex virus, varicella-zoster virus, cytomegalovirus, Epstein-Barr virus), rotaviruses, Norwalk viruses, hantavirus, arenavirus, rhabdovirus (e.g. rabies virus), retroviruses (including HIV, HTLV-I and -II), papovaviruses (e.g. papillomavirus), polyomaviruses, and picornaviruses, and the like), and bacteria (including a wide variety of pathogenic and non-pathogenic prokaryotes of interest including Bacillus; Vibrio, e.g. *V. cholerae*; Escherichia, e.g. Enterotoxigenic *E. coli*, Shigella, e.g. *S. dysenteriae*; Salmonella, e.g. *S. typhi*; Mycobacterium e.g. *M. tuberculosis, M. leprae*; Clostridium, e.g. *C. botulinum, C. tetani, C. difficile, C. perfringens*; Cornyebacterium, e.g. *C. diphtheriae*; Streptococcus, *S. pyogenes, S. pneumoniae*; Staphylococcus, e.g. *S. aureus*; Haemophilus, e.g. *H. influenzae*; Neisseria, e.g. *N. meningitidis, N. gonorrhoeae*; Yersinia, e.g. *G. lamblia Y. pestis*, Pseudomonas, e.g. *P. aeruginosa, P. putida*; Chlamydia, e.g. *C. trachomatis*; Bordetella, e.g. *B. pertussis*; Treponema, e.g. *T. palladium*; and the like) may be used.

In a preferred embodiment, the targeting moiety is all or a portion (e.g. a binding portion) of a ligand for a cell surface receptor. Suitable ligands include, but are not limited to, all or a functional portion of the ligands that bind to a cell surface receptor selected from the group consisting of insulin receptor (insulin), insulin-like growth factor receptor (including both IGF-1 and IGF-2), growth hormone receptor, glucose transporters (particularly GLUT 4 receptor), transferrin receptor (transferrin), epidermal growth factor receptor (EGF), estrogen receptor (estrogen); low density lipoprotein receptor, high density lipoprotein receptor, leptin receptor, interleukin receptors including IL-1, IL-2, IL-3, IL-4, IL-5, IL-6, IL-7, IL-8, IL-9, IL-11, IL-12, IL-13, IL-15, and IL-17 receptors, human growth hormone receptor, VEGF receptor (VEGF), PDGF receptor (PDGF), transforming growth factor receptor (including TGF-$\alpha$ and TGF-$\beta$), EPO receptor (EPO), TPO receptor (TPO), ciliary neurotrophic factor receptor, prolactin receptor, and T-cell receptors. In particular, hormone ligands are preferred. Hormones include both steroid hormones and proteinaceous hormones, including, but not limited to, epinephrine, thyroxine, oxytocin, insulin, thyroid-stimulating hormone, calcitonin, chorionic gonadotropin, cortictropin, follicle-stimulating hormone, glucagon, leuteinizing hormone, lipotropin, melanocyte-stimutating hormone, norepinephrine, parathryroid hormone, thyroid-stimulating hormone (TSH), vasopressin, enkephalins, seratonin, estradiol, progesterone, testosterone, cortisone, and glucocorticoids and the hormones above. Receptor ligands include ligands that bind to receptors such as cell surface receptors, which include hormones, lipids, proteins, glycoproteins, signal transducers, growth factors, cytokines, and others.

In a preferred embodiment, the targeting moiety is a carbohydrate. By "carbohydrate" herein is meant a compound with the general formula Cx(H2O)y. Monosaccharides, disaccharides, and oligo- or polysaccharides are all included within the definition and comprise polymers of various sugar molecules linked via glycosidic linkages. Particularly preferred carbohydrates are those that comprise all or part of the carbohydrate component of glycosylated proteins, including monomers and oligomers of galactose, mannose, fucose, galactosamine, (particularly N-acetylglucosamine), glucosamine, glucose and sialic acid, and in particular the glycosylation component that allows binding to certain receptors such as cell surface receptors. Other carbohydrates comprise monomers and polymers of glucose, ribose, lactose, raffinose, fructose, and other biologically significant carbohydrates. In particular, polysaccharides (including, but not limited to, arabinogalactan, gum arabic, mannan, etc.) have been used to deliver MRI agents into cells; see U.S. Pat. No. 5,554,386, hereby incorporated by reference in its entirety.

In a preferred embodiment, the targeting moiety is a lipid. "Lipid" as used herein includes fats, fatty oils, waxes, phospholipids, glycolipids, terpenes, fatty acids, and glycerides, particularly the triglycerides. Also included within the definition of lipids are the eicosanoids, steroids and sterols, some of which are also hormones, such as prostaglandins, opiates, and cholesterol.

In addition, as will be appreciated by those in the art, any moiety which may be utilized as a TAAGM can be used as a targeting moiety. Particularly preferred in this regard are enzyme inhibitors, as they will not be cleaved off and will serve to localize the MRI agent in the location of the enzyme.

In a preferred embodiment, the targeting moiety may be used to either allow the internalization of the MRI agent to the cell cytoplasm or localize it to a particular cellular compartment, such as the nucleus.

In a preferred embodiment, the targeting moiety is all or a portion of the HIV-1 Tat protein, and analogs and related proteins, which allows very high uptake into target cells. See for example, Fawell et al., PNAS USA 91:664 (1994); Frankel et al., Cell 55:1189 (1988); Savion et al., J. Biol. Chem. 256:1149 (1981); Derossi et al., J. Biol. Chem. 269:10444 (1994); and Baldin et al., EMBO J. 9:1511 (1990); Watson et al., Biochem. Pharmacol. 58:1521 (1999); all of which are incorporated by reference.

In a preferred embodiment, the targeting moiety is a nuclear localization signal (NLS). NLSs are generally short, positively charged (basic) domains that serve to direct the moiety to which they are attached to the cell's nucleus. Numerous NLS amino acid sequences have been reported including single basic NLS's such as that of the SV40 (monkey virus) large T Antigen (Pro Lys Lys Lys Arg Lys Val), Kalderon (1984), et al., Cell, 39:499–509; the human retinoic acid receptor-β nuclear localization signal (ARRRRP); NFκB p50 (EEVQRKRQKL; Ghosh et al., Cell 62:1019 (1990); NFκB p65 (EEKRKRTYE; Nolan et al., Cell 64:961 (1991); and others (see for example Boulikas, J. Cell. Biochem. 55(1):32–58 (1994), hereby incorporated by reference) and double basic NLS's exemplified by that of the Xenopus (African clawed toad) protein, nucleoplasmin (Ala Val Lys Arg Pro Ala Ala Thr Lys Lys Ala Gly Gln Ala Lys Lys Lys Lys Leu Asp), Dingwall, et al., Cell, 30:449–458, 1982 and Dingwall, et al., J. Cell Biol., 107:641–849; 1988). Numerous localization studies have demonstrated that NLSs incorporated in synthetic peptides or grafted onto reporter proteins not normally targeted to the cell nucleus cause these peptides and reporter proteins to be concentrated in the nucleus. See, for example, Dingwall, and Laskey, Ann, Rev. Cell Biol., 2:367–390, 1986; Bonnerot, et al., Proc. Natl. Acad. Sci. USA, 84:6795–6799, 1987; Galileo, et al., Proc. Natl. Acad. Sci. USA, 87:458–462, 1990.

In a preferred embodiment, targeting moieties for the hepatobiliary system are used; see U.S. Pat. Nos. 5,573,752 and 5,582,814, both of which are hereby incorporated by reference in their entirety.

Thus, as outlined herein, the MRI agents of the invention comprise a paramagnetic metal ion bound to a chelator, at least one TAAGM and optionally at least one targeting moiety. In a preferred embodiment, the metal ion complexes of the invention have the formula shown in Structure 5:

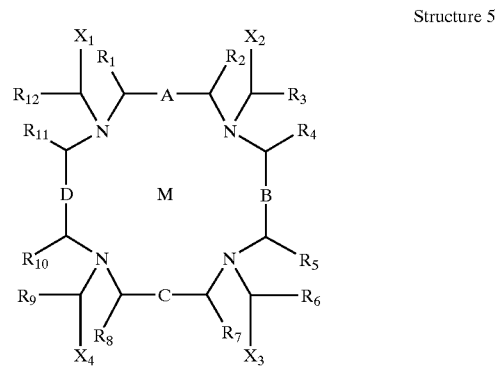

Structure 5

In Structure 5, M is a paramagnetic metal ion selected from the group consisting of Gd(III), Fe(III), Mn(II), Yt(III), and Dy(III). A, B, C and D are each either single or double bonds, with single bonds being preferred; most of the structures depicted herein show single bonds, but this is not to limit the scope of the invention. The $R_1$ through $R_{12}$ groups are substitution groups, including hydrogen, alkyl groups including substituted alkyl groups and heteroalkyl groups as defined below, aryl groups including substituted aryl and heteroaryl groups as defined below, sulfur moieties, amine groups, oxo groups, carbonyl groups, halogens, nitro groups, imino groups, alcohol groups, alkyoxy groups, amido groups, phosphorus moieties, ethylene glycols, ketones, aldehydes, esters, ethers, TAAGMs and targeting moieties, as described above. $X_1$ through $X_4$ are —OH, —COO—, —(CH2)$_n$OH (with —CH$_2$OH being preferred), —(CH2)$_n$COO—(with CH$_2$COO— being preferred), a TAAGM or a targeting moiety. n is from 1 to 10, with from 1 to 5 being preferred. At least one of $R_1$ to $R_{12}$ and $X_1$ to $X_4$ is a TAAGM. Optionally, at least one of $R_1$ to $R_{12}$ and $X_1$ to $X_4$ (different from the TAAGM) is a targeting moiety.

Preferred DOTA embodiments of the invention are depicted below in Structures 6 to 9. These structures are depicted without R groups (although as will be appreciated, any number of R groups as outlined herein can be used), although assuming A, B, C and D are single bonds, there are two hydrogens attached to each carbon. In addition, Structures 6–9 all show an optional targeting moiety.

Structure 6

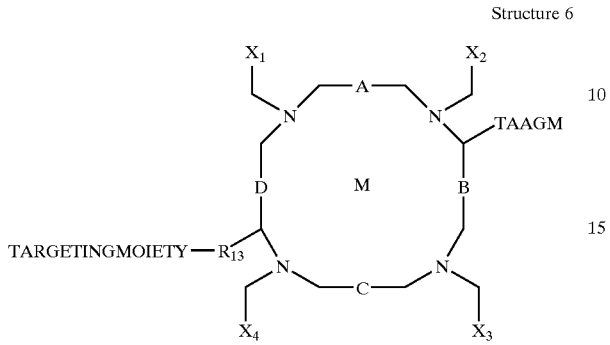

Structure 6 depicts a DOTA derivative with the TAAGM and the optional targeting moiety attached to the carbons of the macrocycle and on "opposite" sides of the molecule. R13 is an optional linker, described herein. As will be appreciated by those in the art, these moieties may be attached to any two carbon atoms of the macrocycle.

Structure 7

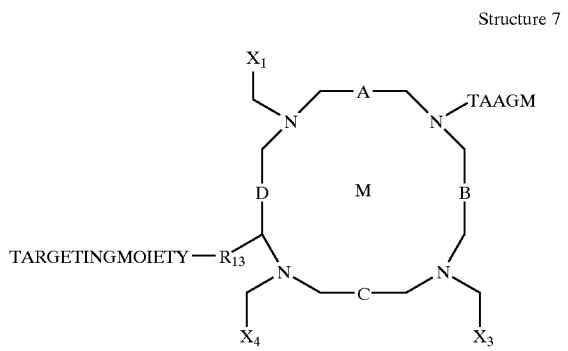

Structure 7 depicts the TAAGM as replacing one of the carboxylic "arms" and an optional targeting moiety, again with a n optional R13 linker, on the opposite side of the molecule. Again, any combination of "arm" and macrocycle carbon may be used, as will be appreciated by those in the art.

Structure 8

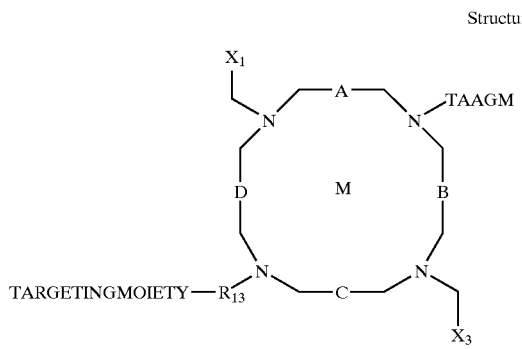

Structure 8 depicts both the TAAGM and the targeting moiety joined to "arms" of the macrocycle. Again, any two "arms" may be used.

Structure 9

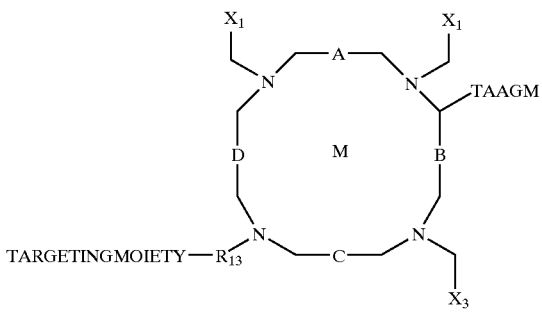

Structure 9 depicts the targeting moiety replacing an arm of the macrocycle and the TAAGM on a carbon of the macrocycle. Again, any two positions may be used.

As applied to DOTA, a preferred embodiment utilizes the four nitrogens of the DOTA ring, and the $X_1$–$X_4$ groups to provide 8 of the coordination atoms for the paramagnetic metal ion. The ninth coordination atom is provided by a TAAGM which is substituted at one of the $R_1$ to $R_{12}$ positions. A targeting moiety is present at a different $R_1$ to $R_{12}$ position. In a preferred embodiment, the other R groups are either hydrogen or methyl; in a particularly preferred embodiment the chelator is Gd-MCTA, which has a single methyl group on the DOTA ring (see Meyer et al., Invest. Radiol. 25:S53 (1990)).

An additional preferred embodiment utilizes the four nitrogens of the DOTA ring, and three of the X groups to provide 7 of the coordination atoms for the paramagnetic metal ion. The remaining coordination atoms are provided by a TAAGM which is substituted at the remaining X position. Alternatively, the coordination sites are either filled by coordination atoms provided by the X groups, or blocked by the X group structure, or both. In addition, some of the structures herein do not depict the A, B, C and D bonds, but as for the other embodiments, these bonds may be either single or double bonds.

In the DOTA-structures depicted herein, any or all of A, B, C or D may be a single bond or a double bond. It is to be understood that when one or more of these bonds are double bonds, there may be only a single substitutent group attached to the carbons of the double bond. For example, when A is a double bond, there may be only a single $R_1$ and a single $R_2$ group attached to the respective carbons; in a preferred embodiment, as described below, the $R_1$ and $R_2$ groups are hydrogen. In a preferred embodiment, A is a single bond, and it is possible to have two $R_1$ groups and two $R_2$ groups on the respective carbons. In a preferred embodiment, these groups are all hydrogen with the exception of a single TAAGM and a single targeting moiety, but alternate embodiments utilize two R groups which may be the same or different. That is, there may be a hydrogen and a blocking group attached in the $R_1$ position, and two hydrogens, two alkyl groups, or a hydrogen and an alkyl group in the $R_2$ positions, etc.

It is to be understood that the exact composition of the $X_1$–$X_4$ groups will depend on the presence of the metal ion. That is, in the absence of the metal ion, the groups may be —OH, —COOH, —(CH$_2$)$_n$OH, or (CH$_2$)$_n$COOH; however, when the metal is present, the groups may be —OH, —COO—, —(CH$_2$)$_n$O—, or (CH$_2$)$_n$COO—.

In preferred embodiments, there is a single TAAGM attached to the metal ion complex. That is, all but one of the R groups are hydrogen. It should be appreciated that the TAAGM and targeting moiety may be at any of the R positions.

Preferred DTPA embodiments of the invention are depicted below in Structures 10 to 14. These structures are depicted without non-hydrogen R groups, although in preferred embodiments there are two hydrogens attached to each carbon. In addition, as for the DOTA structures, a variety of different combinations of sites can be used; two arms, an arm and a carbon of the chelate, etc.

Structure 10

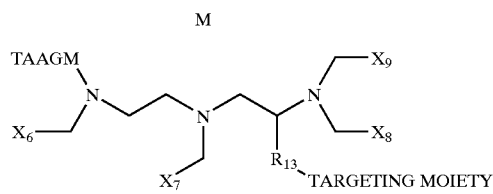

In Structure 10, M is a paramagnetic metal ion selected from the group consisting of Gd(III), Fe(III), Mn(II), Yt(III), and Dy(III). A, B, C and D are each either single or double bonds. The $R_{14}$ through $R_{22}$ groups are substitution groups, including hydrogen, alkyl groups including substituted alkyl groups and heteroalkyl groups as defined below, aryl groups including substituted aryl and heteroaryl groups as defined below, sulfur moieties, amine groups, oxo groups, carbonyl groups, halogens, nitro groups, imino groups, alcohol groups, alkyoxy groups, amido groups, phosphorus moieties, ethylene glycols, ketones, aldehydes, esters, ethers, TAAGMs and targeting moieties as described above. $X_5$ through $X_9$ are —OH, —COO—, —(CH2)$_n$OH (with —CH$_2$OH being preferred), —(CH2)$_n$COO—(with CH$_2$COO—being preferred), a TAAGM or a targeting moiety. n is from 1 to 10, with from 1 to 5 being preferred. At least one of $R_{14}$ to $R_{22}$ and $X_5$ to $X_9$ is a TAAGM. Optionally, at least one of $R_{14}$ to $R_{22}$ and $X_5$ to $X_9$ (different from the TAAGM) is a targeting moiety.

Structure 11

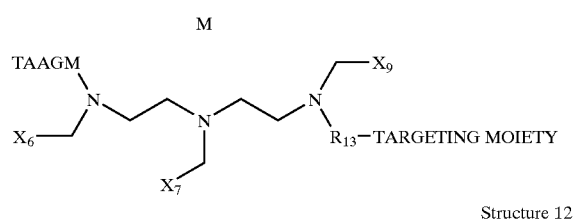

Structure 12

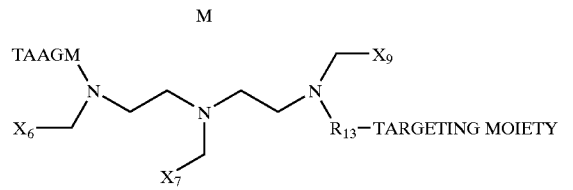

-continued

Structure 13

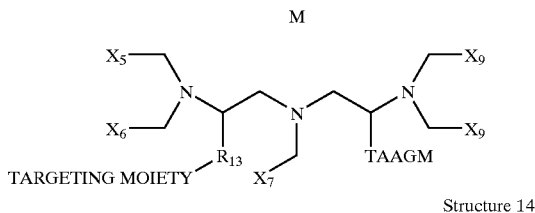

Structure 14

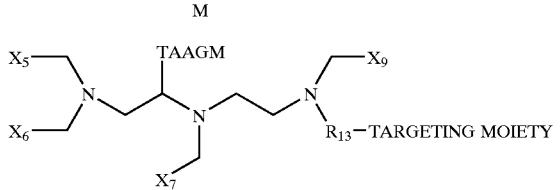

As will be appreciated by those in the art, the MRI compositions of the invention may take on a wide variety of different conformations, as outlined herein. In a preferred embodiment, the MRI agents are "monomers" as depicted in Structures 3–14. Alternatively, in a preferred embodiment, the MRI contrast agents of the invention comprise more than one metal ion, such that the signal is increased. As is outlined below, this may be done in a number of ways. FIG. 6 generally depicts a variety of different configurations of the present invention.

In a preferred embodiment, the MRI agents of the invention comprise at least two paramagnetic metal ions, each with a chelator and TAAGM; that is, multimeric MRI agents are made. In a preferred embodiment, the chelators are linked together, either directly or through the use of a linker such as a coupling moiety or polymer. For example, using substitution groups that serve as functional groups for chemical attachment on the chelator, attachment to other chelators may be accomplished. As will be appreciated by those in the art, attachment of more than one MRI agent may also be done via the TAAGMs (or coordination site barriers, etc.), although these are generally not preferred.

In one embodiment, the chelators are linked together directly, using at least one functional group on each chelator. In this embodiment, the chelators of the invention include one or more substitution groups that serve as functional groups for chemical attachment. Suitable functional groups include, but are not limited to, amines (preferably primary amines), carboxy groups, and thiols (including SPDP, alkyl and aryl halides, maleimides, α-haloacetyls, and pyridyl disulfides) are useful as functional groups that can allow attachment.

This may be accomplished using any number of stable bifunctional groups well known in the art, including homobifunctional and heterobifunctional linkers (see Pierce Catalog and Handbook, 1994, pages T155–T200, hereby expressly incorporated by reference). This may result in direct linkage, for example when one chelator comprises a primary amine as a functional group and the second comprises a carboxy group as the functional group, and carbodiimide is used as an agent to activate the carboxy for attach by the nucleophilic amine (see Torchilin et al., *Critical Rev. Therapeutic Drug Carrier Systems*, 7(4):275–308 (1991). Alternatively, as will be appreciated by those in the art, the use of some bifunctional linkers results in a short coupling moiety being present in the structure. A "coupling moiety" is capable of covalently linking two or more entities. In this embodiment, one end or part of the coupling moiety is attached to the first MRI contrast agent, and the other is attached to the second MRI agent. The functional group(s) of the coupling moiety are generally attached to additional atoms, such as alkyl or aryl groups (including hetero alkyl and aryl, and substituted derivatives), to form the coupling moiety. Oxo linkers are also preferred. As will be appreciated by those in the art, a wide range of coupling moieties are possible, and are generally only limited by the ability to synthesize the molecule and the reactivity of the functional group. Generally, the coupling moiety comprises at least one carbon atom, due to synthetic requirements; however, in some embodiments, the coupling moiety may comprise just the functional group.

In a preferred embodiment, the coupling moiety comprises additional atoms as a spacer. As will be appreciated by those in the art, a wide variety of groups may be used. For example, a coupling moiety may comprise an alkyl or aryl group substituted with one or more functional groups. Thus, in one embodiment, a coupling moiety containing a multiplicity of functional groups for attachment of multiple MRI contrast agents may be used, similar to the polymer embodiment described below. For example, branched alkyl groups containing multiple functional groups may be desirable in some embodiments.

In an additional embodiment, the linker is a polymer. In this embodiment, a polymer comprising at least one MRI contrast agent of the invention is used. As will be appreciated by those in the art, these MRI contrast agents may be monomeric (i.e. one metal ion, one chelator, one TMGM) or a duplex or dimer, as is generally described below (i.e. two metal ions, two chelators, one TAAGM). The targeting moieties can be added to the individual monomers, individual dimers (or multimers), or to the polymer. Preferred embodiments utilize a plurality of MRI agents per polymer. The number of MRI agents per polymer will depend on the density of MRI agents per unit length and the length of the polymer.

The character of the polymer will vary, but what is important is that the polymer either contain or can be modified to contain functional groups for the the attachment of the MRI contrast agents of the invention. Suitable polymers include, but are not limited to, functionalized dextrans, styrene polymers, polyethylene and derivatives, polyanions including, but not limited to, polymers of heparin, polygalacturonic acid, mucin, nucleic acids and their analogs including those with modified ribose-phosphate backbones, the polypeptides polyglutamate and polyaspartate, as well as carboxylic acid, phosphoric acid, and sulfonic acid derivatives of synthetic polymers; and polycations, including but not limited to, synthetic polycations based on acrylamide and 2-acrylamido-2-methylpropanetrimethylamine, poly(N-ethyl-4-vinylpyridine) or similar quarternized polypyridine, diethylaminoethyl polymers and dextran conjugates, polymyxin B sulfate, lipopolyamines, poly(allylamines) such as the strong polycation poly(dimethyidiallylammonium chloride), polyethyleneimine, polybrene, spermine, spermidine and polypeptides such as protamine, the histone polypeptides, polylysine, polyarginine and polyornithine; and mixtures and derivatives of these. Particularly preferred polycations are polylysine and spermidine, with the former being especially preferred. Both optical isomers of polylysine can be used. The D isomer has the advantage of having long-term resistance to cellular proteases. The L isomer has the advantage of being more rapidly cleared from the subject. As will be appreciated by those in the art, linear and branched polymers may be used. A preferred polymer comprising a poly(alkylene oxide is also described in U.S. Pat. No. 5,817,292, incorporated by reference.

A preferred polymer is polylysine, as the —NH$_2$ groups of the lysine side chains at high pH serve as strong nucleophiles for multiple attachment of activated chelating agents. At high pH the lysine monomers are coupled to the MRI agents under conditions that yield on average 5–20% monomer substitution.

In some embodiments, particularly when charged polymers are used, there may be a second polymer of opposite charge to the first that is electrostatically associated with the first polymer, to reduce the overall charge of polymer-MRI agent complex. This second polymer may or may not contain MRI agents.

The size of the polymer may vary substantially. For example, it is known that some nucleic acid vectors can deliver genes up to 100 kilobases in length, and artificial chromosomes (megabases) have been delivered to yeast. Therefore, there is no general size limit to the polymer. However, a preferred size for the polymer is from about 10 to about 50,000 monomer units, with from about 2000 to about 5000 being particularly preferred, and from about 3 to about 25 being especially preferred. In addition, polymers of chelates with a mean molecular weight of between 10–40 kDA serve to distinguish between malignant and benign tumors; see WO 96/35456, hereby incorporated by reference in its entirety.

It should be understood that the multimeric MRI agents of the invention may be made in a variety of ways, including those listed above. What is important is that manner of attachment does not significantly alter the functionality of the agents; that is, the agents must still be "off" in the absence of the cancer target substance and "on" in its presence.

In addition, as will be appreciated by those in the art, when multimeric (all the same monomers) or oligomeric (different monomers)compositions are made, the multimer or oligomer may have one or more targeting moieties. That is, each chelate may comprise a targeting moiety, or a single oligomer, comprising a plurality of chelates, can have a single targeting moiety; alternatively, less than 1 per chelate may be used but more than 1 per oligomer.

In a preferred embodiment, the MRI contrast agents of the invention are "duplexes". In this embodiment, the MRI duplex comprises two chelators, each with a paramagnetic metal ion, and at least one TAAGM that restricts the exchange of water in at least one coordination site of each chelator. In this way, a sort of signal amplification occurs, with two metal ions increasing the signal with a single target molecule. While "duplex" implies two chelators, it is intended to refer to complexes comprising a single TAAGM donating coordination atoms to more than 1 metal ion/chelator complex. As will be appreciated by those in the art, the MRI agents of this embodiment may have a number of different conformations, as is generally shown in FIG. 6. As will be appreciated by those in the art, the $R_{26}$, $R_{27}$ and $R_{28}$ groups of the figure can be attached to any of the positions described herein, to any R groups or $X_1$–$X_4$.

As outlined above, the MRI duplex moieties may also be combined into higher oligomers, either by direct linkage or via attachment to a polymer.

In a preferred embodiment, the metal ion complexes of the present invention are water soluble or soluble in aqueous solution. By "soluble in aqueous solution" herein is meant that the MRI agent has appreciable solubility in aqueous solution and other physiological buffers and solutions. Solubility may be measured in a variety of ways. In one embodiment, solubility is measured using the United States Pharmacopeia solubility classifications, with the metal ion complex being either very soluble (requiring less than one part of solvent for 1 part of solute), freely soluble (requiring one to ten parts solvent per 1 part solute), soluble (requiring ten to thirty parts solvent per 1 part solute), sparingly soluble (requiring 30 to 100 parts solvent per 1 part solute), or slightly soluble (requiring 100–1000 parts solvent per 1 part solute).

Testing whether a particular metal ion complex is soluble in aqueous solution is routine, as will be appreciated by those in the art. For example, the parts of solvent required to solubilize a single part of MRI agent may be measured, or solubility in gm/ml may be determined.

The complexes of the invention are generally synthesized using well known techniques. See, for example, Moi et al., supra; Tsien et al., supra; Borch et al., J. Am. Chem. Soc., p2987 (1971); Alexander, (1995), supra; Jackels (1990), supra, U.S. Pat. Nos. 5,155,215, 5,087,440, 5,219,553, 5,188,816, 4,885,363, 5,358,704, 5,262,532; Meyer et al., (1990), supra, Moi et al., (1988), and McMurray et al., Bioconjugate Chem. 3(2):108–117 (1992)).

For DOTA derivatives, the synthesis depends on whether nitrogen substitution or carbon substitution of the cyclen ring backbone is desired. For nitrogen substitution, such as is exemplified by the galactose-DOTA structures of the examples, the synthesis begins with cyclen or cyclen derivatives, as is well known in the art; see for example U.S. Pat. Nos. 4,885,363 and 5,358,704. FIGS. 3 and 4 depict the nitrogen substitution as exemplified by galactose-DOTA derivatives.

For carbon substitution well known techniques are used. See for example Moi et al., supra, and Gansow, supra.

The contrast agents of the invention are complexed with the appropriate metal ion as is known in the art. While the structures depicted herein all comprise a metal ion, it is to be understood that the contrast agents of the invention need not have a metal ion present initially. Metal ions can be added to water in the form of an oxide or in the form of a halide and treated with an equimolar amount of a contrast agent composition. The contrast agent may be added as an aqueous solution or suspension. Dilute acid or base can be added if need to maintain a neutral pH. Heating at temperatures as high as 100° C. may be required.

The complexes of the invention can be isolated and purified, for example using HPLC systems.

Pharmaceutical compositions comprising pharmaceutically acceptable salts of the contrast agents can also be prepared by using a base to neutralize the complexes while they are still in solution. Some of the complexes are formally uncharged and do not need counterions.

Once made, the compositions of the invention find use in a variety of applications. In particular, the metal ion complexes of the invention have use as magnetic resonance imaging contrast or enhancement agents for use in the diagnosis, imaging or monitoring of cancer in particular.

The metal ion complexes of the invention may be used in a similar manner to the known gadolinium MRI agents. See for example, Meyer et al., supra; U.S. Pat. No. 5,155,215; U.S. Pat. No. 5,087,440; Margerstadt et al., Magn. Reson. Med. 3:808 (1986); Runge et al., Radiology 166:835 (1988); and Bousquet et al., Radiology 166:693 (1988). The metal ion complexes are administered to a cell, tissue or patient as is known in the art. A "patient" for the purposes of the present invention includes both humans and other animals and organisms, such as experimental animals. Thus the methods are applicable to both human therapy and veterinary applications. In addition, the metal ion complexes of the invention may be used to image tissues or cells; for example, see Aguayo et al., Nature 322:190 (1986).

The administration of the agents of the present invention can be done in a variety of ways, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the composition may be directly applied as a solution or spray. Depending upon the manner of introduction, the compounds may be formulated in a variety of ways. The concentration of therapeutically active compound in the formulation may vary from about 0.1–100 wt. %.

The pharmaceutical compositions of the present invention comprise an MRI agent in a form suitable for administration to a patient. In the preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

In addition, in one embodiment, the MRI agents are added in a micellular formulation; see U.S. Pat. No. 5,833,948, hereby incorporated by reference.

Combinations of the compositions may be administered. Moreover, the compositions may be administered in combination with other therapeutics or imaging agents.

Generally, sterile aqueous solutions of the contrast agent complexes of the invention are administered to a patient in a variety of ways, including orally, intrathecally and especially intravenously in concentrations of 0.003 to 1.0 molar, with dosages from 0.03, 0.05, 0.1, 0.2, and 0.3 millimoles per kilogram of body weight being preferred. Dosages may depend on the structures to be imaged.

Suitable dosage levels for similar complexes are outlined in U.S. Pat. Nos. 4,885,363 and 5,358,704.

In addition, the contrast agents of the invention may be delivered via specialized delivery systems, for example, within liposomes (see Navon, Magn. Reson. Med. 3:876–880 (1986)) or microspheres, which may be selectively taken up by different organs (see U.S. Pat. No. 5,155,215).

In some embodiments, it may be desirable to increase the blood clearance times (or half-life) of the MRI agents of the invention. This has been done, for example, by adding carbohydrate polymers, including polyethylene glycol, to the chelator (see U.S. Pat. No. 5,155,215 and 5,605,672). Thus, one embodiment utilizes polysaccharides as substitution R groups on the compositions of the invention.

A preferred embodiment utilizes complexes which cross the blood-brain barrier. Thus, as is known in the art, a DOTA derivative which has one of the carboxylic acids replaced by an alcohol to form a neutral DOTA derivative has been shown to cross the blood-brain barrier. Thus, for example, neutral complexes are designed that cross the blood-brain barrier.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference.

We claim:
1. An MRI agent having the formula:

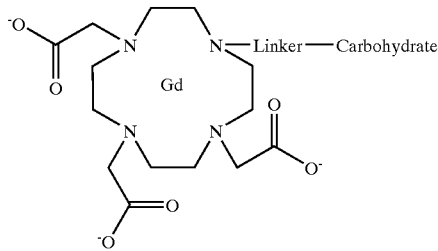

wherein said linker is selected from the group consisting of aryl or alkyl groups; and,
wherein said carbohydrate binds β-glucuronidase.

2. An MRI agent having the formula:

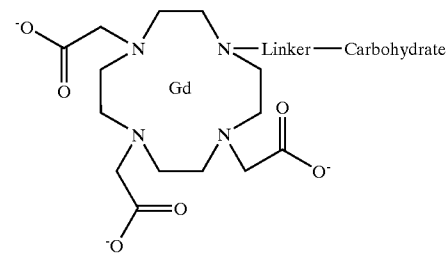

wherein said linker is selected from the group consisting of aryl or alkyl groups; and,
wherein upon interaction with β-glucuronidase, the $T_1$ of the agent is decreased.

3. An MRI agent having the following formula:

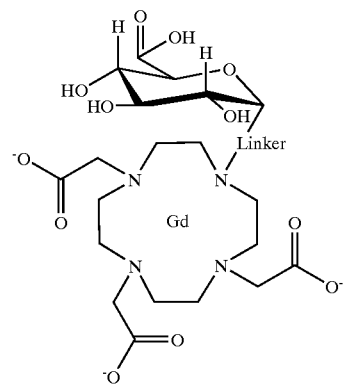

wherein said linker is selected from the group consisting of aryl or alkyl groups.

4. An MRI agent having the following formula:

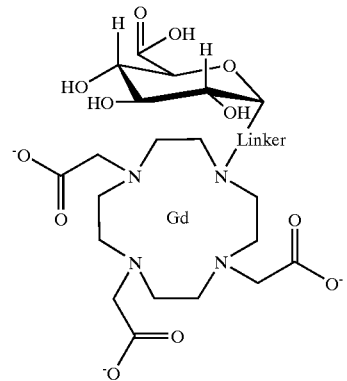

wherein said linker is selected from the group consisting of aryl or alkyl groups; and wherein upon interaction of the β-glucuronide moiety with β-glucuronidase, the $T_1$ of the agent is decreased.

5. An MRI agent according to claim 1, 2, 3 or 4 wherein said linker is an aryl or alkyl group selected from the group consisting of substituted alkyl, heteroalkyl, substituted heteroalkyl, substituted aryl, heteroaryl and substituted heteroaryl.

6. An MRI agent according to claim 1, 2, 3, or 4 wherein said linker is selected from the group consisting of p-aminobenzyl, methyl, ethyl, propyl, butyl, pentyl, hexyl, acetic acid, propionic acid, aminobutyl, p-alkyl phenols, 4-alkylimidazole and glycol.

7. An MRI agent having the following formula:

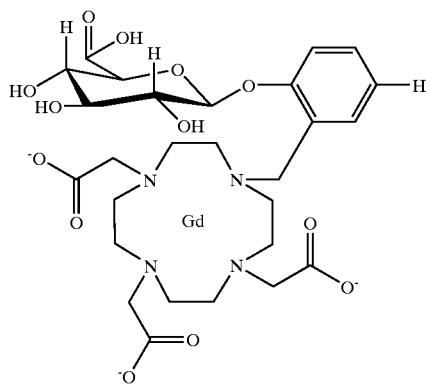

8. A composition comprising an MRI agent according to 1, 2, 3, 4, or 7 and a pharmaceutically acceptable carrier.

9. A method of magnetic resonance imaging of a cell tissue or patient comprising administering an MRI agent according to claim 1, 2, 3, 4, or 7 to a cell, tissue or patient and rendering a magnetic resonance image of said cell, tissue or patient.

10. A method of detecting target substances associated with cancer comprising administering an MRI agent according to claim 1, 2, 3, 4, or 7 to a cell, tissue or patient to produce a magnetic resonance image of said cell, tissue or patient.

* * * * *

UNITED STATES PATENT AND TRADEMARK OFFICE
CERTIFICATE OF CORRECTION

PATENT NO.    : 6,673,333 B1
DATED         : January 6, 2004
INVENTOR(S)   : Thomas J. Meade et al.

It is certified that error appears in the above-identified patent and that said Letters Patent is hereby corrected as shown below:

Column 2,
After the first paragraph, insert the following new paragraph:
 -- The United States Government has certain rights in this invention pursuant to grant number AR-42671 from the National Institutes of Health. --

Signed and Sealed this

Eighteenth Day of May, 2004

JON W. DUDAS
*Acting Director of the United States Patent and Trademark Office*